(12) United States Patent
Sato

(10) Patent No.: US 11,717,269 B2
(45) Date of Patent: Aug. 8, 2023

(54) ULTRASOUND DIAGNOSIS APPARATUS, MEDICAL IMAGE PROCESSING APPARATUS, AND STORAGE MEDIUM

(71) Applicant: CANON MEDICAL SYSTEMS CORPORATION, Otawara (JP)

(72) Inventor: Takeshi Sato, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 733 days.

(21) Appl. No.: 16/560,656

(22) Filed: Sep. 4, 2019

(65) Prior Publication Data
US 2020/0069294 A1 Mar. 5, 2020

(30) Foreign Application Priority Data

Sep. 5, 2018 (JP) ................. 2018-165660

(51) Int. Cl.
| | | |
|---|---|---|
| *A61B 8/06* | (2006.01) | |
| *A61B 8/08* | (2006.01) | |
| *G01S 7/52* | (2006.01) | |
| *A61B 8/14* | (2006.01) | |

(52) U.S. Cl.
CPC .............. *A61B 8/5276* (2013.01); *A61B 8/14* (2013.01); *G01S 7/52077* (2013.01)

(58) Field of Classification Search
CPC ........... A61B 8/06; A61B 8/14; A61B 8/0891; A61B 8/5207; A61B 8/5276; G01S 7/52077; G01S 15/8977; G01S 15/8951
See application file for complete search history.

(56) References Cited

U.S. PATENT DOCUMENTS

| | | |
|---|---|---|
| 5,671,744 A | 9/1997 | Abe et al. |
| 2006/0084874 A1 | 4/2006 | Imamura et al. |
| 2014/0039317 A1 | 2/2014 | Sato |

(Continued)

FOREIGN PATENT DOCUMENTS

| | | |
|---|---|---|
| JP | 8-107896 A | 4/1996 |
| JP | 3683943 B2 | 8/2005 |

(Continued)

OTHER PUBLICATIONS

Hiroki Takahashi, et al., "Echo motion imaging with adaptive clutter filter for assessment of cardiac blood flow", Japanese Journal of Applied Physics, vol. 54, No. 7, 2015, 9 pages (pp. 07HF09-1-07HF09-8 and cover page).

(Continued)

*Primary Examiner* — Boniface Ngathi N
(74) *Attorney, Agent, or Firm* — Oblon, McClelland, Maier & Neustadt, L.L.P.

(57) ABSTRACT

An ultrasound diagnosis apparatus according to an embodiment includes processing circuitry. The processing circuitry is configured to sequentially obtain eigenvalues of a correlation matrix of a scan range, the correlation matrix being obtained from a data sequence of reflected-wave data in mutually the same position acquired by performing an ultrasound scan on the scan range formed with a plurality of scanning lines. The processing circuitry is configured to determine a filter coefficient to be applied to a Moving Target Indicator (MTI) filter, on a basis of the plurality of eigenvalues obtained at mutually-different points in time.

10 Claims, 13 Drawing Sheets

(56) References Cited

U.S. PATENT DOCUMENTS

2015/0320395 A1\* 11/2015 Sato ................ A61B 8/488
                                                    600/455
2015/0366540 A1   12/2015 Sato
2016/0089115 A1\*  3/2016 Sato ................ A61B 8/06
                                                    600/447

FOREIGN PATENT DOCUMENTS

| JP | 3724846 B2    | 12/2005 |
|----|---------------|---------|
| JP | 2006-141994 A | 6/2006  |
| JP | 2014-42823 A  | 3/2014  |
| JP | 2014-158698 A | 9/2014  |
| JP | 2016-2379 A   | 1/2016  |
| JP | 2017-63977 A  | 4/2017  |

OTHER PUBLICATIONS

Alfred C.H. Yu., et al., "Eigen-Based Clutter Filter Design for Ultrasound Color Flow Imaging: A Review", IEEE Transactions on Ultrasonics, Ferroelectrics, and Frequency Control, vol. 57, No. 5, May 2010, 17 pages.

Japanese Office Action dated Jun. 7, 2022 in Japanese Patent Application No. 2018-165660, 3 pages.

Japanese Office Action dated Nov. 22, 2022 in Japanese Patent Application 2018-165660 filed on Sep. 5, 2018, citing reference 15 therein (total 3 pages).

\* cited by examiner

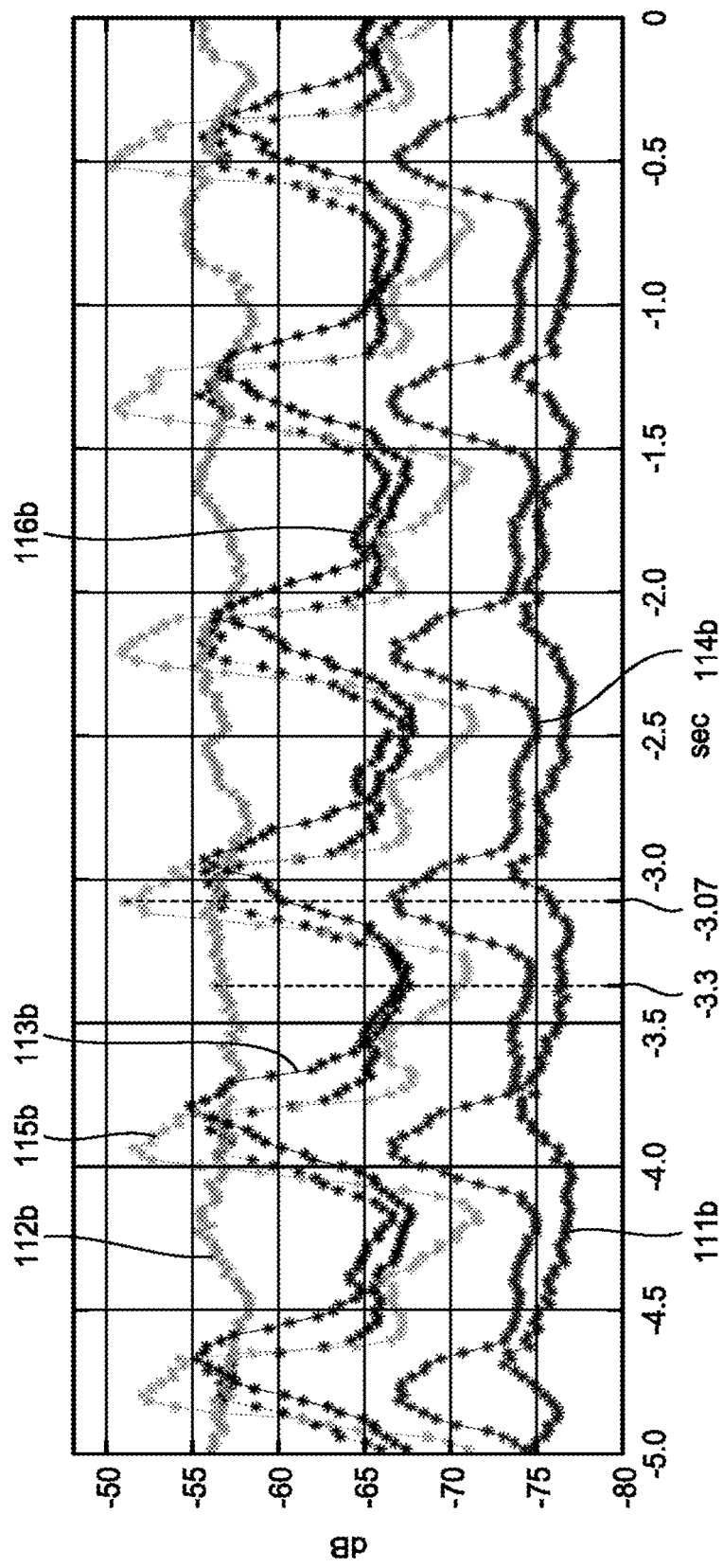

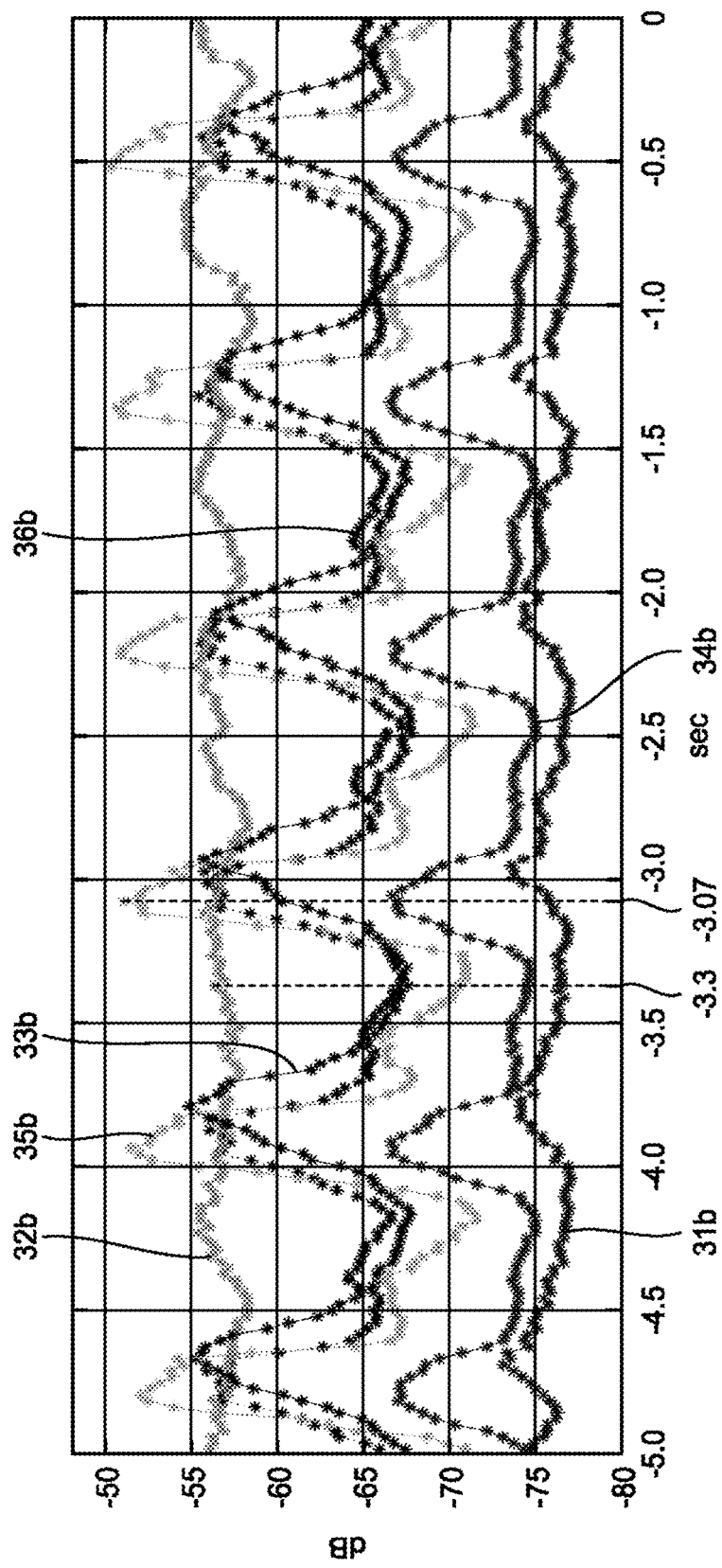

ULTRASOUND DIAGNOSIS APPARATUS, MEDICAL IMAGE PROCESSING APPARATUS, AND STORAGE MEDIUM

CROSS-REFERENCE TO RELATED APPLICATIONS

This application is based upon and claims the benefit of priority from Japanese Patent Application No. 2018-165660, filed on Sep. 5, 2018; the entire contents of which are incorporated herein by reference.

FIELD

Embodiments described herein relate generally to an ultrasound diagnosis apparatus, a medical image processing apparatus, and a storage medium.

BACKGROUND

In recent years, in relation to Color Flow Mapping (CFM) methods, a method has been developed to make it possible to display small blood flows which have a low flow rate slower than motion in the subject's body and which conventional methods were unable to display due to hindrance by tissues of the subject. For example, a blood flow picture method employing an adaptive Moving Target Indicator (MTI) filter using eigenvectors is known. As examples of such a blood flow picture method, a method is known by which a correlation matrix is calculated for an entire image so as to apply one MTI filter matrix to the entire image, and another method is also known by which an imaging target range is divided into a plurality of regions, so as to calculate a correlation matrix for each of the regions and to apply a different one of MTI filter matrices to each of the regions.

However, when a blood flow in the heart is subject to an observation, or when the liver or the like being impacted by the motion of the heart is subject to an observation, clutter caused by the motion of the heart may impact the data output from the MTI filter, for example. As a method for eliminating such clutter being in synchronization with the pulsating motion of the heart, a method is known by which a filter coefficient used for an MTI filter (the filter coefficient applied to the MTI filter) is varied in synchronization with an electrocardiographic (ECG) waveform. Further, another method is also known by which the moving velocity and dispersion of a cardiac wall are calculated by implementing a Tissue Doppler Imaging (TDI) method, so as to adaptively change a cutoff frequency of an MTI filter on the basis of the moving velocity and the dispersion of the cardiac wall.

BRIEF DESCRIPTION OF THE DRAWINGS

FIG. 4 is a graph illustrating an example of temporal changes in the magnitudes of eigenvalues in an S-th place with respect to regions;

FIG. 10C is a graph illustrating an example of temporal changes in the magnitude of an eigenvalue in the S-th place in each of the medium blocks;

DETAILED DESCRIPTION

An ultrasound diagnosis apparatus according to an embodiment includes processing circuitry. The processing circuitry is configured to sequentially obtain eigenvalues of a correlation matrix of a scan range, the correlation matrix being obtained from a data sequence of reflected-wave data in mutually the same position acquired by performing an ultrasound scan on the scan range formed with a plurality of scanning lines. The processing circuitry is configured to determine a filter coefficient to be applied to a Moving Target Indicator (MTI) filter, on a basis of the plurality of eigenvalues obtained at mutually-different points in time.

Exemplary embodiments of an ultrasound diagnosis apparatus, a medical image processing apparatus, and a computer-readable storage medium storing therein a computer program (hereinafter, simply "program") will be explained below, with reference to the accompanying drawings. Possible embodiments are not limited to the embodiments described below. Further, the description of each of the embodiments is, in principle, similarly applicable to any other embodiment.

First Embodiment

Figure 1:
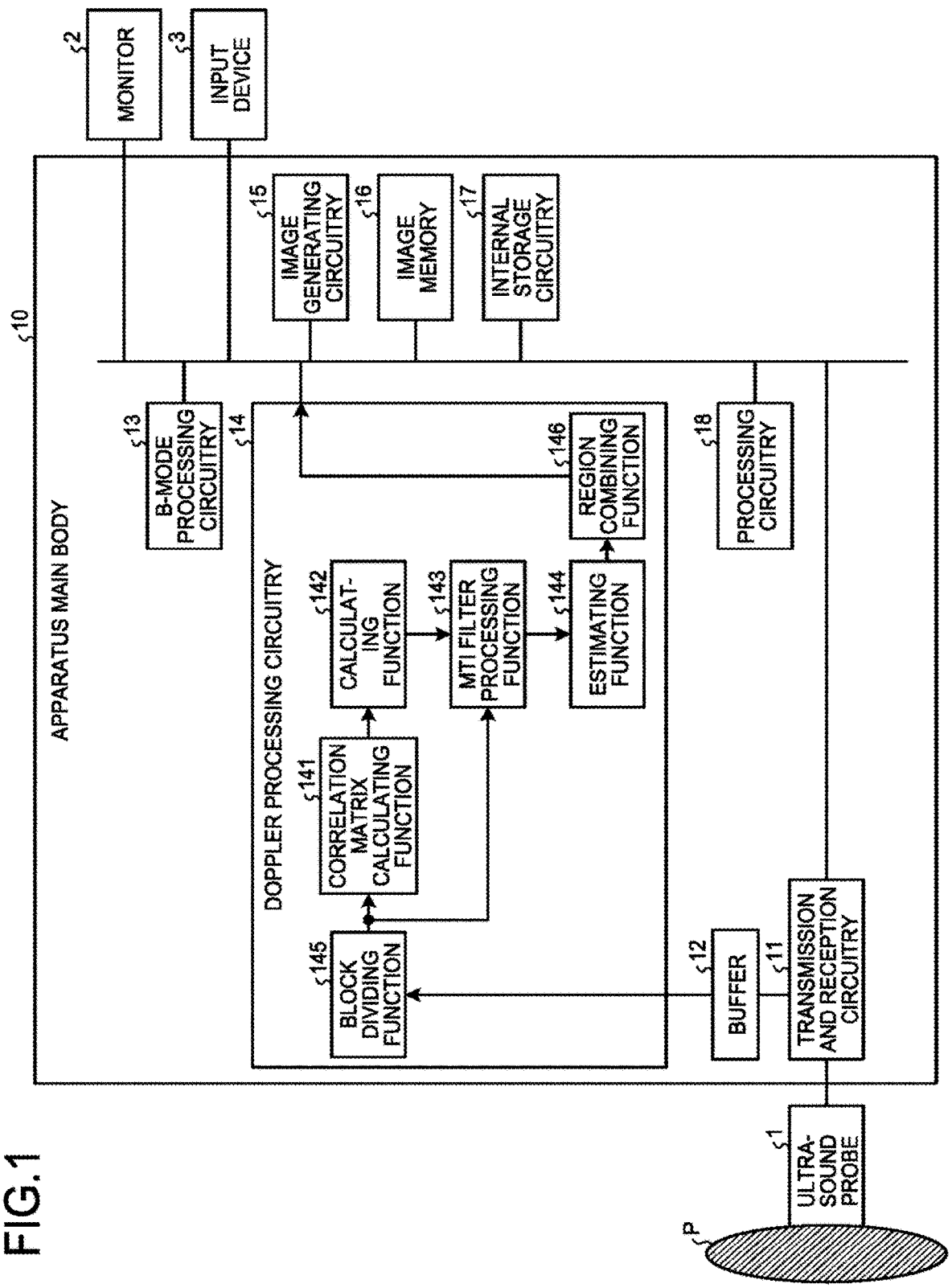
FIG. 1 is a block diagram illustrating an exemplary configuration of an ultrasound diagnosis apparatus according to a first embodiment.

To begin with, a configuration of an ultrasound diagnosis apparatus according to a first embodiment will be explained. FIG. 1 is a block diagram illustrating an exemplary configuration of the ultrasound diagnosis apparatus according to the first embodiment. As illustrated in FIG. 1, the ultrasound diagnosis apparatus according to the first embodiment includes an ultrasound probe 1, a monitor 2, an input device 3, and an apparatus main body 10.

To transmit and receive ultrasound waves, the ultrasound probe 1 is connected to the apparatus main body 10. The ultrasound probe 1 includes a plurality of piezoelectric transducer elements, for example. Each of the plurality of piezoelectric transducer elements is configured to generate an ultrasound wave on the basis of a drive signal (a drive pulse) supplied thereto from transmission and reception circuitry 11 included in the apparatus main body 10. Further, each of the plurality of piezoelectric transducer elements included in the ultrasound probe 1 is configured to receive a reflected wave (echo) from an examined subject P, to convert the received reflected wave into an electric signal (a reflected-wave signal), and to transmit the reflected-wave signal to the apparatus main body 10. Further, the ultrasound probe 1 includes a matching layer provided for the piezoelectric transducer elements, as well as a backing member or the like that prevents the ultrasound waves from propagating rearward from the piezoelectric transducer elements. The ultrasound probe 1 is detachably connected to the apparatus main body 10.

When an ultrasound wave is transmitted from the ultrasound probe 1 to the subject P, the transmitted ultrasound wave is repeatedly reflected on a surface of discontinuity of acoustic impedances at a tissue in the body of the subject P and is received as a reflected wave by each of the plurality of piezoelectric transducer elements included in the ultrasound probe 1. The amplitude of each of the received reflected waves is dependent on the difference between the acoustic impedances on the surface of discontinuity on which the ultrasound wave is reflected. When a transmitted ultrasound pulse is reflected on the surface of a moving blood flow, a cardiac wall, or the like, the reflected wave is, due to the Doppler effect, subject to a frequency shift, depending on a velocity component of the moving members with respect to the ultrasound wave transmission direction.

The first embodiment is applicable to situations where the ultrasound probe 1 is a one-dimensional (1D) array probe that two-dimensionally scans the subject P and where the ultrasound probe 1 is a mechanical four-dimensional (4D) probe or a two-dimensional (2D) array probe that three-dimensionally scans the subject P.

The input device 3 is realized by using a mouse, a keyboard, a button, a panel switch, a touch command screen, a foot switch, a trackball, a joystick, and/or the like. The input device 3 is configured to receive various types of setting requests from an operator of the ultrasound diagnosis apparatus and to transfer the received various types of setting requests to the apparatus main body 10.

The monitor 2 is configured to display a Graphical User Interface (GUI) used by the operator of the ultrasound diagnosis apparatus for inputting the various types of setting requests through the input device 3 and to display an ultrasound image represented by ultrasound image data generated by the apparatus main body 10, and the like. The monitor 2 is realized by using a liquid crystal monitor, a Cathode Ray Tube (CRT) monitor, or the like.

The apparatus main body 10 is a device configured to generate the ultrasound image data on the basis of the reflected-wave signals transmitted thereto from the ultrasound probe 1. The apparatus main body 10 illustrated in FIG. 1 is a device capable of generating two-dimensional ultrasound image data on the basis of two-dimensional reflected-wave signals and capable of generating three-dimensional ultrasound image data on the basis of three-dimensional reflected-wave signals. It should be noted, however, that the first embodiment is also applicable to the situation where the apparatus main body 10 is a device dedicated for two-dimensional data.

As illustrated in FIG. 1, the apparatus main body 10 includes the transmission and reception circuitry 11, a buffer 12, B-mode processing circuitry 13, Doppler processing circuitry 14, image generating circuitry 15, an image memory 16, internal storage circuitry 17, and processing circuitry 18.

The transmission and reception circuitry 11 is configured to control ultrasound scans performed by the ultrasound probe 1 on the basis of instructions from the processing circuitry 18 (explained later). The ultrasound scans denote ultrasound transmissions and receptions, for example. The transmission and reception circuitry 11 includes a pulse generator, a transmission delay circuit, a pulser, and the like and is configured to supply the drive signal to the ultrasound probe 1. The pulse generator is configured to repeatedly generate a rate pulse used for forming a transmission ultrasound wave at a predetermined repetition frequency (a Pulse Repetition Frequency [PRF]). Further, the transmission delay circuit is configured to apply a delay time period that is required to converge the ultrasound waves generated from the ultrasound probe 1 into the form of a beam and to determine transmission directionality and that corresponds to each of the piezoelectric transducer elements, to each of the rate pulses generated by the pulse generator. The pulser is configured to apply the drive signal to the ultrasound probe 1 with timing based on the rate pulses. In other words, by varying the delay time periods applied to the rate pulses, the transmission delay circuit arbitrarily adjusts the transmission directions of the ultrasound waves transmitted from the surfaces of the piezoelectric transducer elements.

The transmission and reception circuitry 11 has a function that is able to instantly change the transmission frequency, the transmission drive voltage, and the like, for the purpose of executing a predetermined scan sequence on the basis of an instruction from the processing circuitry 18. In particular, the function to change the transmission drive voltage is realized by using a linear-amplifier-type transmission circuit of which the value can be instantly switched or by using a mechanism configured to electrically switch between a plurality of power source units.

For example, under the control of the processing circuitry 18, the transmission and reception circuitry 11 causes the ultrasound probe 1 to perform an ultrasound scan for acquiring an inter-frame data sequence as a Doppler data sequence (see, for example, Japanese Patent No. 3724846, Japanese Patent Application Laid-open No. 2014-42823, etc.). For example, under the control of the processing circuitry 18, the transmission and reception circuitry 11 causes the ultrasound probe 1 to perform a first ultrasound scan to obtain information about motion of moving members in a first scan range and causes the ultrasound probe 1 to perform, in a time-division manner during the first ultrasound scan, an ultrasound scan on each of a plurality of sectioned ranges obtained by dividing a second scan range into sections, as a second ultrasound scan to obtain information about a tissue shape in the second scan range. In this situation, the first ultrasound scan may be an ultrasound scan by which the same scanning line is scanned once in one frame.

Further, the transmission and reception circuitry 11 includes an amplifying circuit, an Analog/Digital (A/D) converter, a reception delay circuit, an adder, a quadrature detecting circuit, and the like and is configured to generate the reflected-wave data by performing various types of processes on the reflected-wave signals transmitted from the ultrasound probe 1. Further, the transmission and reception circuitry 11 is configured to store the generated reflected-wave data into the buffer 12. The amplifying circuit is configured to amplify the reflected-wave signals for each of the channels and to perform a gain correcting process. The A/D converter is configured to perform an A/D conversion on the gain-corrected reflected-wave signals. The reception delay circuit is configured to apply a reception delay time period required to determine reception directionality, to the digital data. The adder is configured to perform an adding process on the reflected-wave signals to which the reception delay time period has been applied by the reception delay circuit. As a result of the adding process performed by the adder, reflected components of the reflected-wave signals that are from the direction corresponding to the reception directionality are emphasized. In this situation, the process of adjusting a phase by delaying the reception for each of the reflected-wave signals corresponding to the elements and adding the results together may be referred to as a phased addition process or a beam forming process.

Further, the quadrature detecting circuit is configured to convert the output signal from the adder into an In-phase signal (an I signal) and a Quadrature-phase signal (a Q signal) that are in a baseband. Further, the quadrature detecting circuit is configured to store the I signal and the Q signal (hereinafter, "IQ signals") into the buffer 12 as the reflected-wave data. Alternatively, the quadrature detecting circuit may convert the output signal from the adder into an analysis signal and store the analysis signal into the buffer 12. The IQ signals or the analysis signal can serve as a signal (a reception signals) including phase information. In the following sections, the reflected-wave data output by the transmission and reception circuitry 11 may be referred to as a reception signal.

When the subject P is to be scanned two-dimensionally, the transmission and reception circuitry 11 causes the ultrasound probe 1 to transmit a two-dimensional ultrasound beam. Further, the transmission and reception circuitry 11 generates two-dimensional reflected-wave data from two-dimensional reflected-wave signals transmitted from the ultrasound probe 1. In contrast, when the subject P is to be scanned three-dimensionally, the transmission and reception circuitry 11 causes the ultrasound probe 1 to transmit a three-dimensional ultrasound beam. Further, the transmission and reception circuitry 11 generates three-dimensional reflected-wave data from three-dimensional reflected-wave signals transmitted from the ultrasound probe 1.

The buffer 12 is a memory configured to temporarily store therein the reflected-wave data generated by the transmission and reception circuitry 11. More specifically, the buffer 12 stores therein the reflected-wave data corresponding to a number of frames or the reflected-wave data corresponding to a number of volumes. For example, the buffer 12 is a First-In/First-Out (FIFO) memory and is configured to store therein reflected-wave data corresponding to a predetermined number of frames under control of the transmission and reception circuitry 11. Further, for example, when reflected-wave data corresponding to one frame is newly generated by the transmission and reception circuitry 11, the buffer 12 discards the reflected-wave data corresponding to one frame that was generated earliest and stores therein the newly-generated reflected-wave data corresponding to the one frame, under the control of the transmission and reception circuitry 11. For example, the buffer 12 is realized by using a semiconductor memory element such as a Random Access Memory (RAM), a flash memory, or the like.

The B-mode processing circuitry 13 and the Doppler processing circuitry 14 are signal processing units configured to perform various types of signal processing processes on the reflected-wave data generated from the reflected-wave signals by the transmission and reception circuitry 11. The B-mode processing circuitry 13 and the Doppler processing circuitry 14 are realized by using one or more processors, for example. The B-mode processing circuitry 13 is configured to generate data (B-mode data) in which the signal intensity at each of a plurality of sampling points is expressed with a degrees of brightness, by reading the reflected-wave data from the buffer 12 and performing a logarithmic amplification, an envelope detecting process, a logarithmic compression, and/or the like on the read reflected-wave data.

By performing a filtering process, the B-mode processing circuitry 13 is capable of varying the frequency band to be rendered in a picture, by varying the detected frequency. By using this function of the B-mode processing circuitry 13, the ultrasound diagnosis apparatus according to the first embodiment is able to implement a harmonic imaging process such as a Contrast Harmonic Imaging (CHI) process. In other words, from the reflected-wave data of the subject P into whom a contrast agent is injected, the B-mode processing circuitry 13 is configured to separate reflected-wave data of a harmonic component (harmonic data or subharmonic data) resulting from reflection by the contrast agent (microbubbles and bubbles) and reflected-wave data of a fundamental wave component (fundamental wave data) resulting from reflection by a tissue in the body of the subject P. From the reflected-wave data of the harmonic component, the B-mode processing circuitry 13 is able to generate B-mode data used for generating contrast-enhanced image data.

Further, by using the filtering function of the B-mode processing circuitry 13, the ultrasound diagnosis apparatus according to the first embodiment is capable of implementing a Tissue Harmonic Imaging (THI) process. In other words, from the reflected-wave data of the subject P, the B-mode processing circuitry 13 is capable of separating either the harmonic data or the subharmonic data, which is the reflected-wave data of the harmonic component. Further, from the reflected-wave data of the harmonic component, the B-mode processing circuitry 13 is capable of generating B-mode data used for generating tissue image data from which a noise component has been eliminated.

Further, when implementing a harmonic imaging process such as the CHI or the THI, the B-mode processing circuitry 13 is capable of extracting the harmonic component by using a method different from the abovementioned method involving the filtering process. During the harmonic imaging process, a picture method called an Amplitude Modulation (AM) method, a Phase Modulation (PM) method, or an AMPM method combining together the AM method and the PM method, is implemented. According to the AM method, the PM method, and the AMPM method, ultrasound wave transmissions having mutually-different amplitude levels or phases are performed multiple times on the same scanning line. As a result, the transmission and reception circuitry 11 generates a plurality of pieces of reflected-wave data for each of the scanning lines and outputs the generated reflected-wave data. Further, the B-mode processing circuitry 13 extracts the harmonic component by performing an addition/subtraction process compliant with the modulation method, on the plurality of pieces of reflected-wave data corresponding to the scanning lines. After that, the B-mode processing circuitry 13 generates B-mode data by performing an envelope detecting process and the like on the reflected-wave data of the harmonic component.

For example, when the PM method is implemented, according to a scan sequence set by the processing circuitry 18, the transmission and reception circuitry 11 causes ultrasound waves having opposite phase polarities and mutually the same amplitude levels (e.g., −1 and 1) to be transmitted twice for each of the scanning lines. Further, the transmission and reception circuitry 11 generates a piece of reflected-wave data resulting from the transmission corresponding to "−1" and another piece of reflected-wave data resulting from the transmission corresponding to "1", so that the B-mode processing circuitry 13 adds the two pieces of reflected-wave data together. As a result, such reflected-wave data is generated from which the fundamental wave component has been eliminated and in which a second harmonic component primarily remains. Further, the B-mode processing circuitry 13 generates THI B-mode data or CHI B-mode data by performing an envelope detecting process and the like on the generated reflected-wave data.

Alternatively, for example, to perform a THI process, a method has been put into practice by which a picture is rendered by using a second harmonic component and a combination tone component included in reflected-wave data. According to the picture rendering method using the combination tone component, for example, the ultrasound probe 1 is caused to transmit a transmission ultrasound wave having a combined waveform obtained by combining together a first fundamental wave of which the center frequency is "f1" and a second fundamental wave of which the center frequency is "f2" higher than "f1". The combined waveform is a waveform obtained by combining together the waveform of the first fundamental wave and the waveform of the second fundamental wave of which the phases have mutually been adjusted, so as to generate the combination tone component having the same polarity as that of the second harmonic component. The transmission and reception circuitry 11 causes the transmission ultrasound wave having the combined waveform to be transmitted twice, for example, while inverting the phase thereof. In that situation, for example, the B-mode processing circuitry 13 extracts the harmonic component from which the fundamental wave component has been eliminated and in which the combination tone component and the second harmonic component primarily remain by adding together the two pieces of reflected-wave data and subsequently performs an envelope detecting process and the like.

By reading the reflected-wave data from the buffer 12 and performing a frequency analysis on the read reflect-wave data, the Doppler processing circuitry 14 is configured to estimate motion information of moving members that are present in the scan range based on the Doppler effect and to generate data (Doppler data) indicating the estimated motion information. For example, as the motion information of the moving members, the Doppler processing circuitry 14 estimates an average velocity value, an average dispersion value, an average power value, and the like for each of the plurality of sampling points and generates the Doppler data indicating the estimated motion information. In this situation, the moving members are for example, a blood flow, a tissue such as the cardiac wall, and the contrast agent. The Doppler processing circuitry 14 according to the present embodiment estimates, as the motion information (blood flow information) of the blood flow, an average velocity value of the blood flow, a dispersion value of the blood flow velocity, a power value of a blood flow signal, and the like for each of the plurality of sampling points and generates Doppler data indicating the estimated blood flow information.

The B-mode processing circuitry 13 and the Doppler processing circuitry 14 are capable of processing both two-dimensional reflected-wave data and three-dimensional reflected-wave data. In other words, the B-mode processing circuitry 13 is configured to generate two-dimensional B-mode data from two-dimensional reflected-wave data and to generate three-dimensional B-mode data from three-dimensional reflected-wave data. Further, the Doppler processing circuitry 14 is configured to generate two-dimensional Doppler data from two-dimensional reflected-wave data and to generate three-dimensional Doppler data from three-dimensional reflected-wave data.

By using the abovementioned function of the Doppler processing circuitry 14, the ultrasound diagnosis apparatus according to the present embodiment is capable of implementing a color Doppler method that may be called a Color Flow Mapping (CFM) method. According to the CFM method, the transmission and reception of an ultrasound wave is performed multiple times on a plurality of scanning lines. Further, according to the CFM method, a signal derived from the blood flow is extracted, while suppressing a signal (a clutter signal) derived from a stationary or slow-moving tissue, by applying a Moving Target Indicator (MTI) filter to a data sequence in mutually the same position. Further, according to the CFM method, blood flow information such as a velocity value of the blood flow, a dispersion value of the blood flow, a power value of the blood flow, and the like is estimated from the blood flow signal. The image generating circuitry 15 (explained later) is configured to generate ultrasound image data (color Doppler image data) that, for example, two-dimensionally displays, in color, a distribution of the estimated result. Further, the monitor 2 is configured to display a color Doppler image represented by the color Doppler image data. The ultrasound image data displaying, in color, the distribution of the estimated result of the blood flow information may be referred to as blood flow image data.

As an MTI filter, it is common practice to use a filter having a fixed coefficient, such as a Butterworth Infinite Impulse Response (IIR) filter, a polynomial regression filter, or the like. In contrast, the Doppler processing circuitry 14 according to the present embodiment uses, as the MTI filter, an adaptive MTI filter that varies the coefficient thereof in accordance with an input signal. More specifically, as the adaptive MTI filter, the Doppler processing circuitry 14 according to the present embodiment uses a filter called "Eigenvector Regression Filter". In the following sections, the "Eigenvector Regression Filter", which is an adaptive MTI filter using eigenvectors, will be referred to as an "eigenvector MTI filter".

The eigenvector MTI filter is configured to calculate an eigenvector from a correlation matrix and to calculate a coefficient used for a clutter component suppressing process from the calculated eigenvector. This method is an application of a method used in a main component analysis, a Karhunen-Loeve transform, or an eigenspace method.

The Doppler processing circuitry 14 according to the first embodiment that employs the eigenvector MTI filter includes, as illustrated in FIG. 1, a correlation matrix calculating function 141, a calculating function 142, an MTI filter processing function 143, an estimating function 144, a block dividing function 145, and a region combining function 146. In this situation, for example, processing functions performed by the constituent elements of the Doppler processing circuitry 14 illustrated in FIG. 1, namely, the correlation matrix calculating function 141, the calculating function 142, the MTI filter processing function 143, the estimating function 144, the block dividing function 145, and the region combining function 146, are recorded in the internal storage circuitry 17 in the form of computer-executable programs (a medical image processing program). The Doppler processing circuitry 14 is realized by using a processor, for example. By reading and executing the programs from the internal storage circuitry 17, the Doppler processing circuitry 14 realizes the functions corresponding to the read programs. In other words, the Doppler processing circuitry 14 that has read the programs has the functions illustrated within the Doppler processing circuitry 14 in FIG. 1.

The correlation matrix calculating function 141 is configured, for example, to calculate a correlation matrix of the scan range from a data sequence of consecutive pieces of reflected-wave data in mutually the same position (the same sampling point). The correlation matrix calculating function 141 is an example of a calculating unit, for example.

The calculating function 142 is configured, for example, to calculate eigenvalues of the correlation matrix and eigenvectors corresponding to the eigenvalues. For example, the calculating function 142 calculates a filter matrix used for suppressing the clutter component from a matrix obtained by reducing the rank of a matrix in which the eigenvectors are arranged on the basis of the magnitudes of the eigenvalues. For example, the calculating function 142 calculates the filter matrix from a matrix in which the eigenvectors are arranged on the basis of the magnitudes of the eigenvalues and of which the rank is reduced on the basis of a result of comparing values indicating the magnitudes of the eigenvalues with a threshold value. For example, the calculating function 142 is an example of a determining unit or an obtaining unit. Further, the filter matrix is an example of a filter coefficient applied to the eigenvector MTI filter.

By using the filter matrix, the MTI filter processing function 143 is configured to output a data sequence obtained by suppressing the clutter component and extracting the blood flow signal derived from the blood flow, from the data sequence of the consecutive pieces of reflected-wave data in mutually the same position (the same sampling point).

The estimating function 144 is configured to estimate the blood flow information by performing a calculation such as an auto-correlation calculation or the like while using the data output by the MTI filter processing function 143 and to output the Doppler data indicating the estimated blood flow information.

The block dividing function 145 is configured to divide the scan range formed with a plurality of scanning lines into a plurality of regions. The region combining function 146 is configured to combine together the pieces of data in the divided regions. Specific processes performed by the Doppler processing circuitry 14 according to the first embodiment will be explained in detail later.

The image generating circuitry 15 is configured to generate the ultrasound image data from the data generated by the B-mode processing circuitry 13 and the Doppler processing circuitry 14. The image generating circuitry 15 generates two-dimensional B-mode image data in which the intensities of the reflected waves are expressed with brightness levels, from the two-dimensional B-mode data generated by the B-mode processing circuitry 13. Further, the image generating circuitry 15 generates two-dimensional Doppler image data in which the blood flow information is rendered in a picture, from the two-dimensional Doppler data generated by the Doppler processing circuitry 14. The two-dimensional Doppler image data is velocity image data, dispersion image data, power image data, or image data combining any of these types of image data. As Doppler image data, the image generating circuitry 15 generates color Doppler image data in which the blood flow information is displayed in color or generates Doppler image data in which one piece of blood flow information is displayed in a gray scale.

In this situation, generally speaking, the image generating circuitry 15 converts (by performing a scan convert process) a scanning line signal sequence from an ultrasound scan into a scanning line signal sequence in a video format used by, for example, television and generates display-purpose ultrasound image data. More specifically, the image generating circuitry 15 generates the display-purpose ultrasound image data by performing a coordinate transformation process compliant with the ultrasound scanning mode used by the ultrasound probe 1. Further, as various types of image processing processes besides the scan convert process, the image generating circuitry 15 performs, for example, an image processing process (a smoothing process) to re-generate an average brightness value image, an image processing process (an edge enhancement process) that uses a differential filter inside an image, or the like, by using a plurality of image frames resulting from the scan convert process. Also, the image generating circuitry 15 combines text information of various types of parameters, scale graduations, body marks, and the like with the ultrasound image data.

In other words, the B-mode data and the Doppler data are each ultrasound image data before the scan convert process. The data generated by the image generating circuitry 15 is the display-purpose ultrasound image data after the scan convert process. The B-mode data and the Doppler data may be referred to as raw data. From two-dimensional ultrasound image data before the scan convert process, the image generating circuitry 15 is configured to generate display-purpose two-dimensional ultrasound image data.

Further, the image generating circuitry 15 is configured to generate three-dimensional B-mode image data by performing a coordinate transformation process on three-dimensional B-mode data generated by the B-mode processing circuitry 13. Further, the image generating circuitry 15 is configured to generate three-dimensional Doppler image data by performing a coordinate transformation process on three-dimensional Doppler data generated by the Doppler processing circuitry 14. The image generating circuitry 15 generates the "three-dimensional B-mode image data and three-dimensional Doppler image data" as "three-dimensional ultrasound image data (volume data)".

Further, the image generating circuitry 15 is configured to perform a rendering process on volume data, to generate any of various types of two-dimensional image data for the purpose of displaying the volume data on the monitor 2. Examples of the rendering process performed by the image generating circuitry 15 include a process of generating Multi Planar Reconstruction (MPR) image data from the volume data, by implementing an MPR method. Further, examples of the rendering process performed by the image generating circuitry 15 also include a Volume Rendering (VR) process to generate two-dimensional image data reflecting three-dimensional information. The image generating circuitry 15 is an example of an image generating unit.

The image memory 16 is a memory configured to store therein the display-purpose image data generated by the image generating circuitry 15. Further, the image memory 16 is also capable of storing therein the data generated by the B-mode processing circuitry 13 and the Doppler processing circuitry 14. After a diagnosis process, for example, the operator is able to invoke any of the B-mode data and the Doppler data stored in the image memory 16. The invoked data can serve as display-purpose ultrasound image data after being routed through the image generating circuitry 15. Further, the image memory 16 is also capable of storing therein the reflected-wave data output by the transmission and reception circuitry 11. For example, the image memory 16 is realized by using a semiconductor memory element such as a RAM, a flash memory, or the like, or a hard disk, or an optical disk.

The internal storage circuitry 17 is configured to store therein a control program for performing the ultrasound wave transmission/reception process, image processing processes, and display processes, diagnosis information (e.g., subjects' IDs and observation of medical doctors) and various types of data such as diagnosis protocols, various types of body marks, and the like. Further, the internal storage circuitry 17 may also be used, as necessary, for storing therein any of the image data stored in the image memory 16. Further, it is possible to transfer any of the data stored in the internal storage circuitry 17 to an external device via an interface (not illustrated). Further, the internal storage circuitry 17 is also capable of storing therein data transferred thereto from an external device via an interface (not illustrated). For example, the internal storage circuitry 17 is realized by using a semiconductor memory element such as a flash memory, a hard disk, or an optical disk.

The processing circuitry 18 is configured to control the entirety of the processes performed by the ultrasound diagnosis apparatus. More specifically, the processing circuitry 18 is configured to control processes of the transmission and reception circuitry 11, the B-mode processing circuitry 13, the Doppler processing circuitry 14, and the image generating circuitry 15, on the basis of the various types of setting requests input by the operator via the input device 3, and any of various types of control programs and various types of data read from the internal storage circuitry 17. For example, the processing circuitry 18 controls ultrasound scans by controlling the ultrasound probe 1 via the transmission and reception circuitry 11. Usually, according to the CFM method, the B-mode image data, which is tissue image data, is displayed together with the color Doppler image data, which is blood flow image data. To realize such display, the processing circuitry 18 causes the ultrasound probe 1 to perform the first ultrasound scan to obtain the blood flow information in the first scan range. The first ultrasound scan is, for example, an ultrasound scan to acquire color Doppler image data in a Doppler mode. Further, the first ultrasound scan is, for example, an ultrasound scan by which the same scanning line is scanned once in one frame.

Further, together with the first ultrasound scan, the processing circuitry 18 causes the ultrasound probe 1 to perform the second ultrasound scan to obtain the information about the tissue shape in the second scan range. The second ultrasound scan is, for example, an ultrasound scan to acquire B-mode image data in a B-mode.

The processing circuitry 18 causes the first ultrasound scan and the second ultrasound scan to be performed by controlling the ultrasound probe 1 via the transmission and reception circuitry 11. In this situation, the first scan range and the second scan range may be the same as each other. The first scan range may be smaller than the second scan range. Conversely, the second scan range may be smaller than the first scan range.

Further, the processing circuitry 18 exercises control so that the monitor 2 displays an ultrasound image represented by any of the display-purpose ultrasound image data stored in the image memory 16 and the internal storage circuitry 17. The transmission and reception circuitry 11 and the like built in the apparatus main body 10 may be configured by using hardware such as an integrated circuit or may be one or more computer programs organized in a module in the manner of software. The processing circuitry 18 is realized by using a processor, for example. The processing circuitry 18 is an example of a controlling unit.

An overall configuration of the ultrasound diagnosis apparatus according to the first embodiment has thus been explained. Next, an ultrasound diagnosis apparatus employing a commonly-used eigenvector MTI filter will be explained as a first comparison example. In the first comparison example, the eigenvector MTI filter has characteristics where the amplitude is relatively large so as to significantly suppress a tissue component (a clutter component) exhibiting uniform motion within a predetermined range.

In the first comparison example, an example will be explained in which the subject of an ultrasound scan is the liver, while side lobe reflection sources are present on the outside of the image range, such as a cardiac wall being a highly reflective member and moving periodically and the diaphragm being a highly reflective member and moving periodically due to an impact of the periodical motion of the heart. In that situation, the cardiac wall and the diaphragm, or the like that are present in the vicinity of the liver reflect a side lobe. The amplitude of the reflected side lobe is relatively not large. Further, the phase of the reflected side lobe changes depending on the position. Accordingly, the motion including the phases (or phase shifts) is not uniform. Further, the amplitude and the phase of the reflected side lobe are close to the amplitude and the phase of a blood flow. For this reason, the suppression of the clutter component by the eigenvector MTI filter may be insufficient, and the side lobe may be extracted by the eigenvector MTI filter as a blood flow signal, in some situations. Such a phenomenon does not constantly occur, but occurs in a predetermined cardiac phase such as during systolic periods, for example, in which the cardiac wall exhibits the steepest changes. As a result, in the first comparison example, the clutter component that was not sufficiently suppressed may periodically be included in a specific region of the ultrasound image data corresponding to a specific cardiac phase, in some situations. For this reason, in a moving image displayed on a monitor, although the blood flow is clearly rendered steadily, a large amount of clutter occurs in the specific region only for a short period of time, in the specific temporal phase once every heartbeat.

Figure 2A:
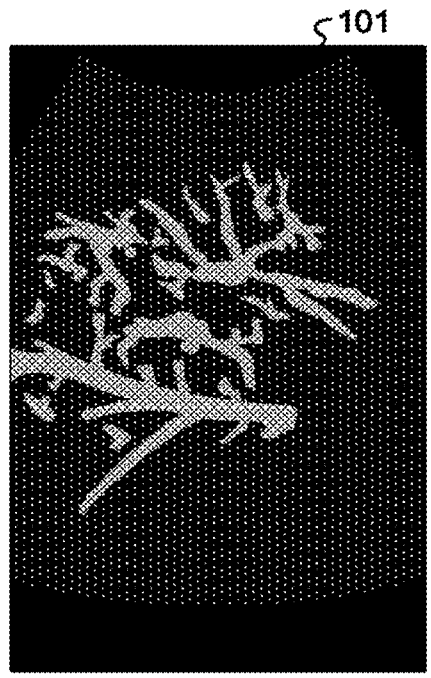
FIG. 2A is a drawing illustrating an example of a blood flow image represented by blood flow image data generated by an ultrasound diagnosis apparatus according to a first comparison example.
Figure 2B:
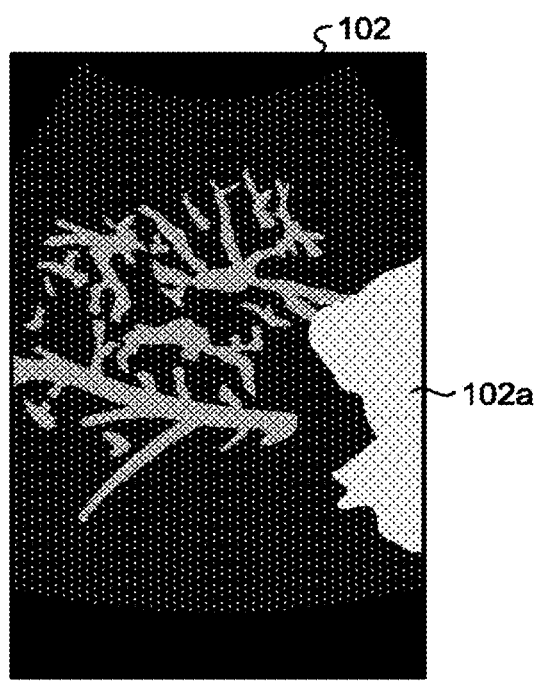
FIG. 2B is another drawing illustrating an example of a blood flow image represented by blood flow image data generated by the ultrasound diagnosis apparatus according to the first comparison example.

FIGS. 2A and 2B are drawings illustrating examples of blood flow images represented by blood flow image data generated by the ultrasound diagnosis apparatus according to the first comparison example. Blood flow images 101 and 102 illustrated in FIGS. 2A and 2B are images rendering blood flow information of the liver of a subject. The blood flow images 101 and 102 are power images generated from power image data. The ultrasound diagnosis apparatus according to the first comparison example is configured to generate the blood flow image data representing the blood flow image 101, by dividing the imaging target range (the scan range) into a plurality of regions, calculating a correlation matrix for each of the regions, and applying a different one of MTI filter matrices to each of the regions. Further, the ultrasound diagnosis apparatus according to the first comparison example is configured to generate the blood flow image data representing the blood flow image 102 by using the same method. More specifically, for example, each of these pieces of blood flow image data is generated by calculating a filter coefficient of an eigenvector MTI filter (an MTI filter coefficient) from eigenvalues and eigenvectors of a correlation matrix obtained by calculating an ensemble average of a data sequence having a packet length (a packet size) of 32, for each of the regions. In this situation, the temporal phase (a first temporal phase) corresponding to the blood flow image 101 and the temporal phase (a second temporal phase) corresponding to the blood flow image 102 are different from each other.

The blood flow image 101 in the first temporal phase has a relatively small amount of clutter throughout the entire image. In contrast, in the blood flow image 102 in the second temporal phase, because the cardiac wall, the diaphragm, and the like that are present on the outside of the image range as reflection sources of a side lobe have large movements, clutter 102a appears in the right section of the blood flow image 102 as illustrated in FIG. 2B.

Figure 3A:
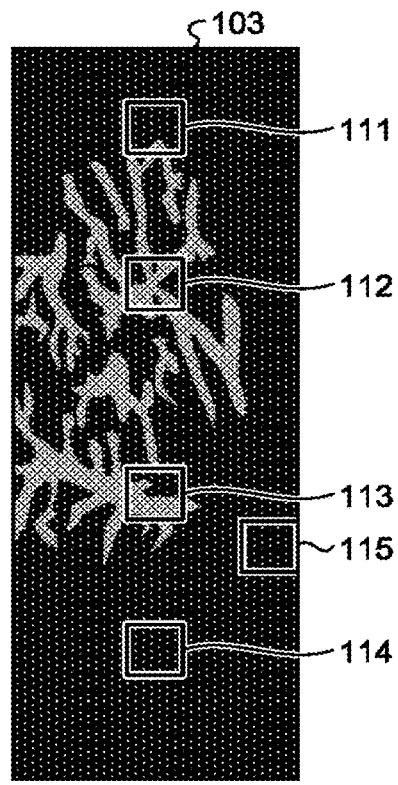
FIG. 3A is a drawing illustrating another example of a blood flow image represented by blood flow image data generated by the ultrasound diagnosis apparatus according to the first comparison example.
Figure 3B:
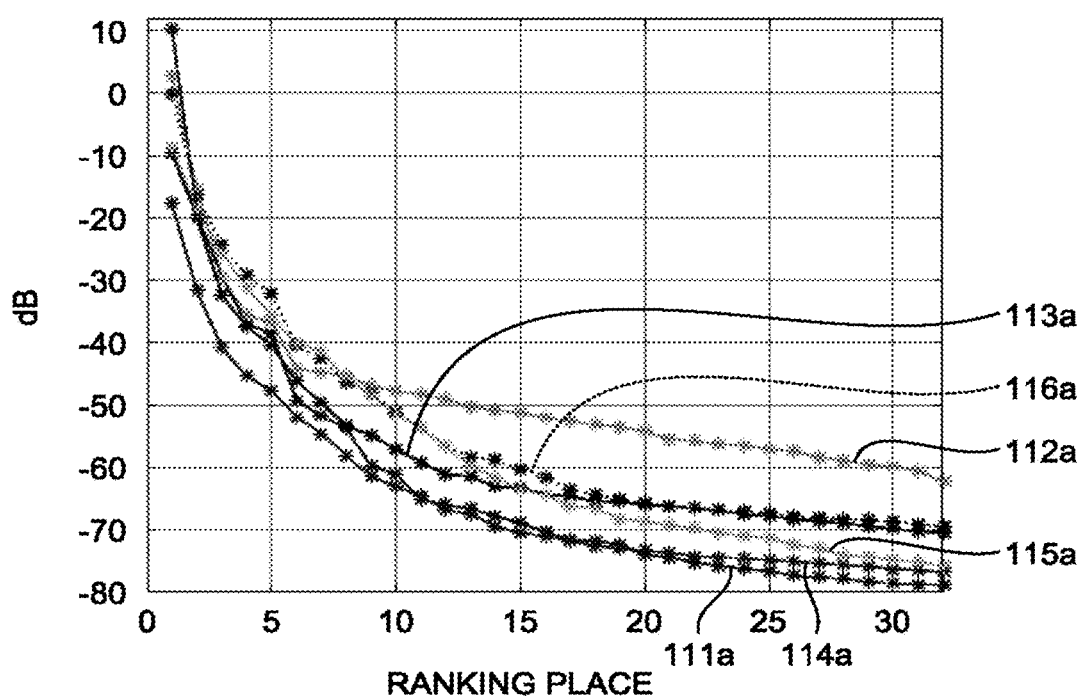
FIG. 3B is a graph illustrating examples of magnitudes of a plurality of eigenvalues of regions calculated at the time of generating the blood flow image data representing the blood flow image in FIG. 3A.
Figure 3C:
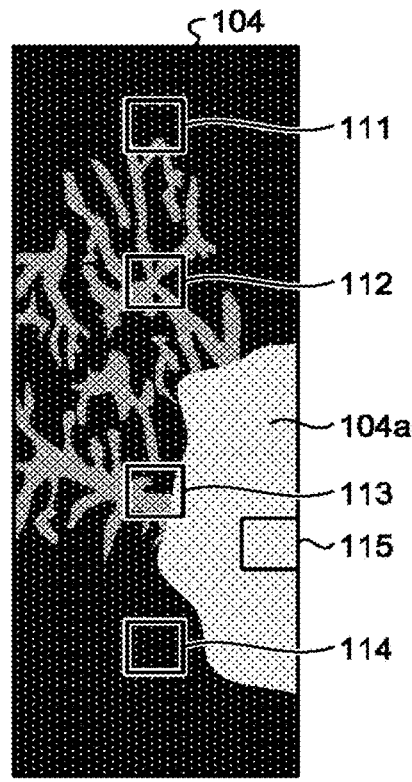
FIG. 3C is a drawing illustrating yet another example of a blood flow image represented by blood flow image data generated by the ultrasound diagnosis apparatus according to the first comparison example.

FIGS. 3A and 3C are drawings illustrating other examples of blood flow images represented by blood flow image data generated by the ultrasound diagnosis apparatus according to the first comparison example. Blood flow images 103 and 104 illustrated in FIGS. 3A and 3C are also images rendering blood flow information of the liver of a subject and are each a power image generated from power image data. By using the same method as the method used for generating the blood flow image data representing the blood flow image 101 illustrated in FIG. 2A, the ultrasound diagnosis apparatus according to the first comparison example generates the blood flow image data representing the blood flow image 103 illustrated in FIG. 3A and the blood flow image data representing the blood flow image 104 illustrated in FIG. 3C. The blood flow images 103 and 104 are images generated from the blood flow image data based on reflected-wave signals acquired by a convex probe and are each an image displayed on a monitor without having a coordinate transformation performed thereon.

In this situation, as explained above, the correlation matrix is calculated for each of the plurality of regions at the time of generating the blood flow images 103 and 104. The five reference numerals 111 to 115 in FIGS. 3A and 3C indicate five regions among the plurality of regions.

The temporal phase (a third temporal phase) corresponding to the blood flow image 103 and the temporal phase (a fourth temporal phase) corresponding to the blood flow image 104 are different from each other. In the third temporal phase, because the motion of the cardiac wall, the diaphragm, and the like that are present on the outside of the image range as reflection sources of a side lobe is relatively small, the blood flow image 103, as a whole, has a relatively small amount of clutter. In contrast, in the fourth temporal phase, because the cardiac wall, the diaphragm, and the like have large movements, a large amount of clutter 104a is included in the right section of the blood flow image 104 as illustrated in FIG. 3C.

Figure 3D:
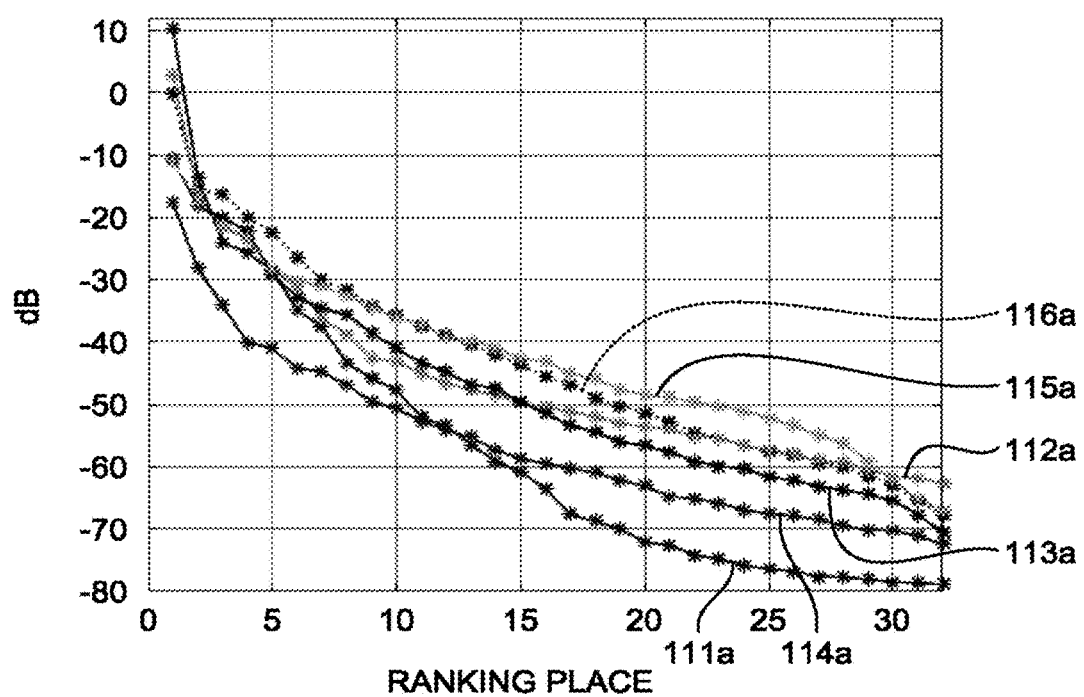
FIG. 3D is a graph illustrating examples of magnitudes of a plurality of eigenvalues of regions calculated at the time of generating the blood flow image data representing the blood flow image in FIG. 3C.

FIG. 3B is a graph illustrating examples of the magnitudes of the plurality of eigenvalues of the regions calculated at the time of generating the blood flow image data representing the blood flow image in FIG. 3A. FIG. 3D is a graph illustrating examples of the magnitudes of the plurality of eigenvalues of the regions calculated at the time of generating the blood flow image data representing the blood flow image in FIG. 3C.

In the graphs in FIGS. 3B and 3D, the horizontal axis expresses ranking places (ranking order) obtained by arranging all the eigenvalues of the regions in descending order of the magnitudes of the eigenvalues. The vertical axis expresses the magnitudes of eigenvalues of the regions in the various ranking places in the unit of decibels, while expressing the largest eigenvalue among the eigenvalues of a correlation matrix obtained by calculating an ensemble average of all the correlation matrices of all the regions as 0 dB.

FIGS. 3B and 3D illustrate graphs of the five regions 111 to 115. More specifically, in FIGS. 3B and 3D, the graph 111a is a graph of the region 111; the graph 112a is a graph of the region 112; the graph 113a is a graph of the region 113; the graph 114a is a graph of the region 114; and the graph 115a is a graph of the region 115. In FIGS. 3B and 3D, the graph 116a is a graph of all the eigenvalues of the correlation matrix obtained by calculating an ensemble average of all the correlation matrices of all the regions.

FIGS. 3B and 3D illustrate graphs 111a to 116a that are obtained by calculating 32 eigenvalues for each of the regions. In other words, each of the graphs 111a to 116a indicates the magnitudes of the eigenvalues in the 1st ranking place (the eigenvalue of which the ranking order is the 1st) to the 32nd ranking place (the eigenvalue of which the ranking order is the 32nd).

Next, the explanation will be continued while a focus is placed on the eigenvalues in the 24th place. In FIG. 3B, the magnitude of the eigenvalue in the 24th place in the graph 112a corresponding to the region 112 is larger than the magnitudes of the eigenvalues in the 24th place in the graphs 111a, 113a, 114a, and 115a corresponding to the other regions 111, 113, 114, and 115. In this situation, by observing the blood flow image 103 in FIG. 3A, it is understood that the region 112 is a region in which blood flow information is rendered.

In contrast, in FIG. 3D, the magnitude of the eigenvalue in the 24th place in the graph 115a corresponding to the region 115 is larger than the magnitudes of the eigenvalues in the 24th place in the graphs 111a to 114a corresponding to the other regions 111 to 114. In this situation, by observing the blood flow image 104 in FIG. 3C, it is understood that the region 115 includes clutter.

FIG. 4 is a graph illustrating an example of temporal changes in the magnitudes of the eigenvalues in the 24th place with respect to the regions. FIG. 4 illustrates graphs 111b to 115b indicating temporal changes over 5 seconds in the magnitudes of the eigenvalues in the 24th place in the five regions 111 to 115, respectively.

More specifically, in FIG. 4, the graph 111b is a graph indicating the temporal changes in the magnitude of the eigenvalue in the 24th place in the region 111; the graph 112b is a graph indicating the temporal changes in the magnitude of the eigenvalue in the 24th place in the region 112; the graph 113b is a graph indicating the temporal changes in the magnitude of the eigenvalue in the 24th place in the region 113; the graph 114b is a graph indicating the temporal changes in the magnitude of the eigenvalue in the 24th place in the region 114; and the graph 115b is a graph indicating the temporal changes in the magnitude of the eigenvalue in the 24th place in the region 115. Further, in FIG. 4, the graph 116b is a graph indicating temporal changes in the magnitude of the eigenvalue in the 24th place among a plurality of eigenvalues of a correlation matrix obtained by calculating an ensemble average of all the correlation matrices of all the regions.

In the graphs, the horizontal axis expresses time (seconds [sec]). On the horizontal axis, the time in the past before the present time is indicated with negative values. For example, the time "0 (sec)" indicates the present time (the current point in time). Further, for example, the time "−0.5 (sec)" indicates the time (the point in time) in the past that is 0.5 seconds earlier than the present time. The vertical axis expresses the magnitude of the eigenvalue in the 24th place for each of the regions in the unit of decibels, while expressing the largest eigenvalue among the plurality of eigenvalues of the correlation matrix obtained by calculating an ensemble average of all the correlation matrices of all the regions as 0 dB.

For example, the third temporal phase corresponding to the blood flow image 103 illustrated in FIG. 3A corresponds to the time "−3.3 (sec)" in FIG. 4. Further, the fourth temporal phase corresponding to the blood flow image 104 illustrated in FIG. 3C corresponds to the time "−3.07 (sec)" in FIG. 4. In other words, the blood flow image data representing the blood flow image 103 is data based on reflected-wave signals acquired at the time "−3.3 (sec)". The blood flow image data representing the blood flow image 104 is data based on reflected-wave signals acquired at the time "−3.07 (sec)".

Next, the explanation will be continued while a focus is placed on the region 115. The region 115 in the blood flow image 103 contains almost no clutter. In contrast, the region 115 in the blood flow image 104 contains a large amount of clutter. This situation is expressed in the graph 115b in FIG. 4 corresponding to the region 115. For example, the graph 115b has some temporal phases (e.g., the time "−3.07 (sec)") in which the eigenvalues are relatively large and other temporal phases (e.g., the time "−3.3 (sec)") in which the eigenvalues are relatively small and indicates that clutter occurs in the temporal phases in which the eigenvalues are relative large and that almost no clutter occurs in the temporal phases in which the eigenvalues are relatively small. It is considered that the temporal phases in which the eigenvalues are relatively large are temporal phases in which the clutter occurs because, for example, the motion of the cardiac wall is relatively large. On the contrary, it is considered that the temporal phases in which the eigenvalues are relatively small are temporal phases in which almost no clutter occurs because, for example, the motion of the cardiac wall is relatively small.

Further, in the graph 115b, the fluctuation of the eigenvalue is relatively large, compared to other graphs 111b to 114b and 116b. Further, the graphs 111b to 116b periodically fluctuate in synchronization with the cardiac cycle of the subject P. Accordingly, the graph 115b periodically exhibits the temporal phases in which the eigenvalues are relatively large and the temporal phases in which the eigenvalues are relatively small. Consequently, the region 115 corresponding to the graph 115b periodically contains clutter.

In relation to this, a method is known (see Patent Literature (Japanese Patent Application Laid-open No. 2014-158698)) and Non Patent Literature (Alfred C. H. Yu, Lasse Lovstakken, "Eigen-Based Clutter Filter Design for Ultrasound Color Flow Imaging: A Review", IEEE Transactions on Ultrasonics, Ferroelectrics, and Frequency Control, vol. 57, no. 5, May 2010)) by which it is judged whether an imaged object is a blood flow or not from ranking order of eigenvalues and the magnitudes (e.g., decibel values) of the eigenvalues. However, as apparent from the above explanation using FIGS. 3A to 3D and 4, it would be difficult to accurately determine whether an imaged object is a blood flow or clutter on the basis of the ranking order and the magnitudes of eigenvalues in one temporal phase. The reason is that the ranking order and the magnitudes of the eigenvalues diversely change depending on attenuation of the ultrasound waves in the subject's body, how much or how little blood flow there is in the surroundings, and the reflection intensity of the tissue. In particular, when clutter is caused by a side lobe, it would be difficult to determine whether an imaged object is a blood flow or clutter on the basis of the eigenvalues.

Further, another method is also possible by which an ultrasound diagnosis apparatus calculates moving velocity and dispersion of a cardiac wall by implementing a Tissue Doppler Imaging (TDI) method, so as to adaptively change a cutoff frequency of an MTI filter on the basis of the moving velocity and the dispersion of the cardiac wall. The ultrasound diagnosis apparatus implementing this method shall be explained as an ultrasound diagnosis apparatus according to a second comparison example. The ultrasound diagnosis apparatus according to the second comparison example, however, observes motion of a tissue having relatively large amplitude by implementing the TDI method. In contrast, the amplitude of a side lobe reflected by a cardiac wall or the diaphragm is relatively not large. For this reason, even when the ultrasound diagnosis apparatus according to the second comparison example implements the abovementioned method by which the cutoff frequency is adaptively changed, the clutter component may not be suppressed sufficiently, in some situations.

To cope with these circumstances, the ultrasound diagnosis apparatus according to the first embodiment is configured to perform the processes described below, to be able to generate an MTI filter capable of suppressing a clutter component occurring as a result of a side robe being reflected by a highly reflective member such as a cardiac wall, the diaphragm, and the like. The ultrasound diagnosis apparatus according to the first embodiment measures temporal changes in the magnitude of an eigenvalue in a predetermined ranking place in each medium block (region) in a time width of one heartbeat or longer and further determines a rankcut number that determines a characteristic of the eigenvector MTI filter on the basis of the difference between a minimum value among the eigenvalues during the time width and the magnitude of the eigenvalue at the present time. In the following sections, the eigenvector MTI filter shall simply be referred to as an "MTI filter".

Figure 5:
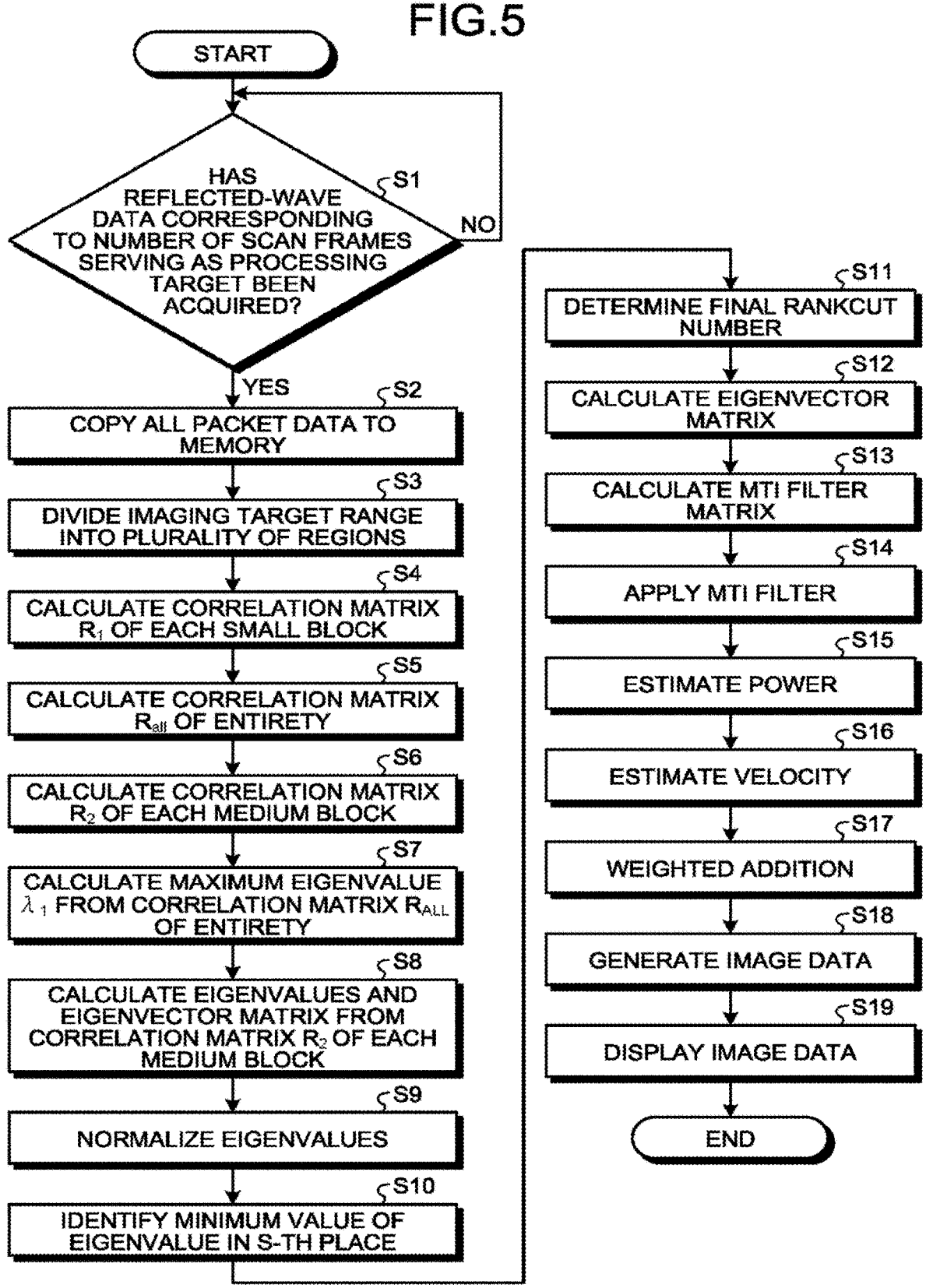
FIG. 5 is a flowchart illustrating a processing procedure performed by the ultrasound diagnosis apparatus according to the first embodiment.

FIG. 5 is a flowchart illustrating a processing procedure performed by the ultrasound diagnosis apparatus according to the first embodiment.

Steps S1 through S3 in FIG. 5 are steps corresponding to the block dividing function 145. Steps S1 through S3 are steps at which the block dividing function 145 is realized as a result of the Doppler processing circuitry 14 invoking and executing a predetermined program corresponding to the block dividing function 145 from the internal storage circuitry 17. At step S1, the block dividing function 145 judges whether or not reflected-wave data corresponding to the number of scan frames serving as a processing target has been acquired (step S1). When having determined that the reflected-wave data corresponding to the number of scan frames has not been acquired (step S1: No), the block dividing function 145 performs the judging process at step S1 again.

On the contrary, when the block dividing function 145 determines that the reflected-wave data corresponding to the number of scan frames has been acquired (step S1: Yes), the process proceeds to step S2.

In the first embodiment, the processes at step S2 and thereafter are performed every time reflected-wave data corresponding to one frame is newly stored into the buffer 12. Further, in the first embodiment, the processes at step S2 and thereafter are performed for each frame in a real-time manner.

At step S2, the block dividing function 145 copies all of the packet data of all the spatial points into a memory. In the present example, the quantity of all the spatial points will be expressed as "$N_{all}$", whereas the packet size will be expressed as "L". For example, the block dividing function 145 copies the input data in the buffer 12 to the memory provided in the Doppler processing circuitry 14. The block dividing function 145 performs the copying operation for each of the invoked packets.

Figure 6:
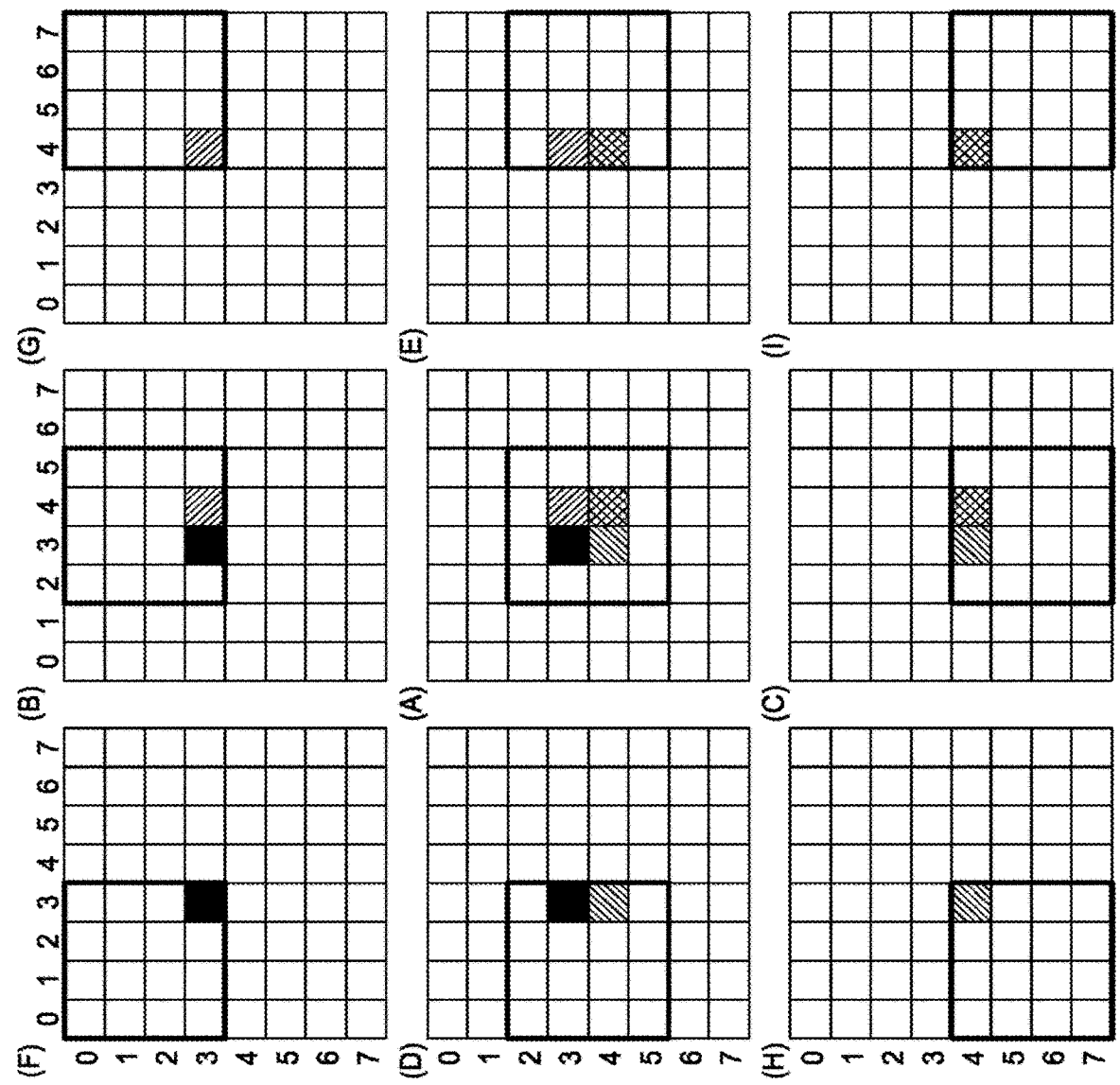
FIG. 6 is a drawing for explaining the first embodiment.

At step S3, the block dividing function 145 divides an imaging target range into a plurality of regions. The imaging target range is an ultrasound scan range, for example. FIG. 6 is a drawing for explaining the first embodiment. FIG. 6 illustrates a partial region of the entire imaging target range. FIG. 6 illustrates examples in which the same region is divided by using nine different dividing patterns, namely (A) to (I).

For example, the block dividing function 145 divides the imaging target range into a plurality of regions so that the small grid boxes in FIG. 6 are the smallest division units. The smallest division units will be referred to as small blocks. In patterns (A) to (I) in FIG. 6, the dividing patterns of the small blocks are the same. In one example, the block dividing function 145 performs the dividing process so that each of the small blocks contains 8 raster and 8 samples. In this situation, the block dividing function 145 divides the spatial region into the small blocks so as to have a number of spatial samples that ensures a degree of freedom (≥the packet length L).

Further, the block dividing function 145 forms a medium block by using two or more of the small blocks. For example, the block dividing function 145 forms the medium block with small blocks in the formation of 4 across and 4 down enclosed in a bold-lined square in FIG. 6. In other words, the medium block is formed with the 4×4 small blocks. In one example, the block dividing function 145 forms the medium block as indicated in each of patterns (A) to (I) in FIG. 6.

The explanation will be continued by using the medium block in the bold-lined square in pattern (A) in FIG. 6 as an example. The medium block in (A) partially overlaps with each of the eight medium blocks, namely the medium blocks in adjacently-positioned pattern (B) to pattern (I). For example, the small block indicated with solid black in (A) is also contained, in duplicate, in the medium blocks in patterns (B), (D), and (F).

In other words, the block dividing function 145 divides the imaging target range into the plurality of medium blocks so that a part of each of the medium blocks overlaps with a part of each of the other medium blocks.

Steps S4 through S6 are steps corresponding to the correlation matrix calculating function 141. Steps S4 through S6 are steps at which the correlation matrix calculating function 141 is realized as a result of the Doppler processing circuitry 14 invoking and executing a predetermined program corresponding to the correlation matrix calculating function 141 from the internal storage circuitry 17. At step S4, the correlation matrix calculating function 141 calculates a correlation matrix $R_1$ in each of the small blocks. When a packet data column vector at a certain location point i is expressed as $x_i$, it is possible to express the correlation matrix $R_1$ by using Expression (1) presented below, where i denotes the position of the certain location point. For example, the single subscript i expresses a position x,z for a two-dimensional scan and expresses a position x,y,z for a three-dimensional scan. The letter N denotes the quantity of the location points in which the calculation is performed. Specifically, the letter N denotes the quantity of all of the location points in each of the small blocks. The letter H denotes a complex conjugate transpose matrix (a Hermitian transpose matrix). When the packet length is expressed as L, the correlation matrix $R_1$ is an L×L matrix.

$$R_1 = \frac{1}{N}\sum_{i=1}^{N} x_i x_i^H \tag{1}$$

The correlation matrix calculating function 141 may calculate the correlation matrix $R_1$ from a packet data column vector $x_1$ acquired over a plurality of frames by performing the abovementioned first ultrasound scan by which the same scanning line is scanned once in one frame. In this situation, the packet data column vector $x_i$ is a data sequence of reflected-wave data in mutually the same position.

At step S5, the correlation matrix calculating function 141 calculates a correlation matrix $R_{all}$ of the entirety by calculating an arithmetic mean of the correlation matrices of all the small blocks. When the total quantity of the small blocks is expressed as $M_{all}$, while an m-th correlation matrix $R_1$ among the $M_{all}$ correlation matrices $R_1$ is expressed as $R_{1,m}$, it is possible to express the correlation matrix $R_{all}$ by using Expression (2) presented below.

$$R_{all} = \frac{1}{M_{all}}\sum_{m=1}^{M_{all}} R_{1,m} \tag{2}$$

In this situation, the correlation matrix calculating function 141 may calculate the correlation matrix $R_{all}$ from the correlation matrix $R_{1,m}$ based on the abovementioned packet data column vector $x_i$ acquired over the plurality of frames. In other words, the correlation matrix calculating function 141 may calculate the correlation matrix $R_{all}$ from the packet data column vector $x_i$ acquired over the plurality of frames.

At step S6, the correlation matrix calculating function 141 calculates a correlation matrix $R_2$ of a medium block. For example, when the quantity of the small blocks contained in one medium block is expressed as $M_2$, while an m-th correlation matrix $R_1$ among the $M_2$ correlation matrices $R_1$ is expressed as $R_{1,m}$, the correlation matrix calculating function 141 calculates the correlation matrix $R_2$ of the medium block by using Expression (3) presented below.

$$R_2 = \frac{1}{M_2} \sum_{m=1}^{M_2} R_{1,m} \quad (3)$$

In this situation, the correlation matrix calculating function 141 may calculate the correlation matrix $R_2$ from the correlation matrix $R_{1,m}$ based on the abovementioned packet data column vector $x_i$ acquired over the plurality of frames. In other words, the correlation matrix calculating function 141 may calculate the correlation matrix $R_2$ from the packet data column vector $x_i$ acquired over the plurality of frames. In that situation, the correlation matrix calculating function 141 obtains a correlation matrix $R_2$ of each of the plurality of medium blocks obtained by dividing the imaging target range into sections, from the data sequence of the reflected-wave data in mutually the same position acquired by performing an ultrasound scan on the imaging target range formed with a plurality of scanning lines. In this situation, the medium blocks serve as an example of the regions into which the imaging target range is divided.

The correlation matrix calculating function 141 calculates the correlation matrix $R_2$ of each of the medium blocks that are each made up of 4×4 small blocks. More specifically, the correlation matrix calculating function 141 divides a correlation matrix obtained by adding together the $M_2$ correlation matrices $R_1$ calculated for the small blocks by $M_2$. In other words, the correlation matrix calculating function 141 calculates the correlation matrix $R_2$ of each of the medium blocks by calculating an arithmetic mean of the correlation matrices $R_1$ of the small blocks in the medium block.

Steps S7 through S13 are steps corresponding to the calculating function 142. Steps S7 through S13 are steps at which the calculating function 142 is realized as a result of the Doppler processing circuitry 14 invoking and executing a predetermined program corresponding to the calculating function 142 from the internal storage circuitry 17. At step S7, the calculating function 142 calculates the largest eigenvalue $\lambda_1$ from the correlation matrix $R_{all}$ of the entirety. More specifically, the calculating function 142 calculates eigenvalues $\lambda$ ($\lambda_1, \lambda_2, \ldots,$ and $\lambda_L$) of which the quantity is equal to L and eigenvectors corresponding to the eigenvalues $\lambda$ by performing an eigenvalue decomposition on the correlation matrix $R_{all}$ by using Expression (4) presented below.

$$R_{all} = VDV^H \quad (4)$$

In Expression (4), the letter V denotes a matrix having eigenvectors as column vectors thereof, whereas the letter D denotes a diagonal matrix having eigenvalues as diagonal elements thereof. Let us assume that the eigenvalues $\lambda$ of which the quantity is equal to L and the eigenvectors corresponding to the eigenvalues $\lambda$ are arranged in descending order. It is possible to express the matrix V by using Expression (5) presented below and to express the matrix D by using Expression (6) presented below. The calculating function 142 uses the largest eigenvalue among the L eigenvalues $\lambda$ as $\lambda_1$.

$$V = \begin{pmatrix} v_{1,1} & v_{1,2} & \cdots & v_{1,L} \\ v_{2,1} & v_{2,2} & & v_{2,L} \\ \vdots & & & \vdots \\ v_{L,1} & v_{L,2} & \cdots & v_{L,L} \end{pmatrix} \quad (5)$$

$$D = \begin{pmatrix} \lambda_1 & 0 & \cdots & 0 \\ 0 & \lambda_2 & & 0 \\ \vdots & & \ddots & \vdots \\ 0 & 0 & \cdots & \lambda_L \end{pmatrix} \quad (6)$$

At step S8, the calculating function 142 calculates eigenvalues and eigenvectors from the correlation matrix $R_2$ of each medium block. In this situation, the calculating function 142 calculates the eigenvalues and the eigenvectors from the correlation matrix $R_2$ of each medium block, by using the same method as the method used for calculating the eigenvalues and the eigenvectors from the correlation matrix $R_{all}$ of the entirety at step S7. In this manner, for example, the calculating function 142 sequentially obtains the eigenvalues and the eigenvectors from the correlation matrix $R_2$ obtained for each of the medium blocks.

At step S9, the calculating function 142 normalizes the eigenvalues. For example, the calculating function 142 normalizes the eigenvalues $\lambda$ of the correlation matrix $R_2$ by dividing, for each of the medium blocks, the eigenvalues $\lambda$ of the correlation matrix $R_2$ by the total power of the correlation matrix $R_{all}$ of the entirety (the sum of all the eigenvalues of the correlation matrix $R_{all}$). As a result, it is possible to eliminate impacts of gains. Alternatively, the calculating function 142 may normalize the eigenvalues $\lambda$ of the correlation matrix $R_2$ by dividing the eigenvalues $\lambda$ by the largest eigenvalue $\lambda_1$ of the correlation matrix $R_{all}$, instead of the normalization using the total power. By performing the normalization by using the largest eigenvalue $\lambda_1$ of the correlation matrix $R_{all}$ of the entire image, it is possible to eliminate gain dependency and impacts from biological tissue differences caused by the division into the regions. The normalized eigenvalues $\lambda$ will be used in the processes at step S10 and thereafter.

At step S10, for each of the medium blocks, the calculating function 142 identifies a minimum value of the eigenvalue in the S-th ranking place among the plurality of eigenvalues in the S-th ranking place with respect to the correlation matrix $R_2$ calculated at step S8, in the predetermined time period (the predetermined time span) from the present time to the time that is 1.2 seconds earlier than the present time. In this situation, the letter "S" is a natural number of 1 to L, inclusive. The letter "L" denotes the packet length. The time period "1.2 seconds" is the duration of one heartbeat when the heartrate of the subject P is 50 beats per minute (bpm). However, the predetermined time period does not necessarily have to be 1.2 seconds and may be any length of time equal to or longer than one heartbeat. It should be noted, however, the longer the predetermined time period is, the more easily the motion of the ultrasound probe 1 held in the hand of an operator will be included in the ultrasound image as noise. For this reason, it is desirable to set the predetermined time period to a length of time of approximately one heartbeat.

Further, the eigenvalue in the S-th place is the S-th eigenvalue in the ranking order when, for example, all the eigenvalues of the correlation matrix $R_2$ are arranged in descending order of the magnitudes of the eigenvalues. In the following sections, an example will be explained in which the ultrasound diagnosis apparatus uses the eigenvalue in the 24th place as an eigenvalue indicating the presence of a blood flow, from among the eigenvalues in the 1st to the 32nd places. In other words, the example will be explained in which "S" is equal to "24", whereas "L" is equal to "32". However, the ultrasound diagnosis apparatus may use an eigenvalue in any other ranking place besides the 24th place, as long as the eigenvalue indicates the presence of the blood flow. For example, the value of the ranking place may be determined depending on the packet length L, the site of the subject's body, or an input from the user.

Figure 7:
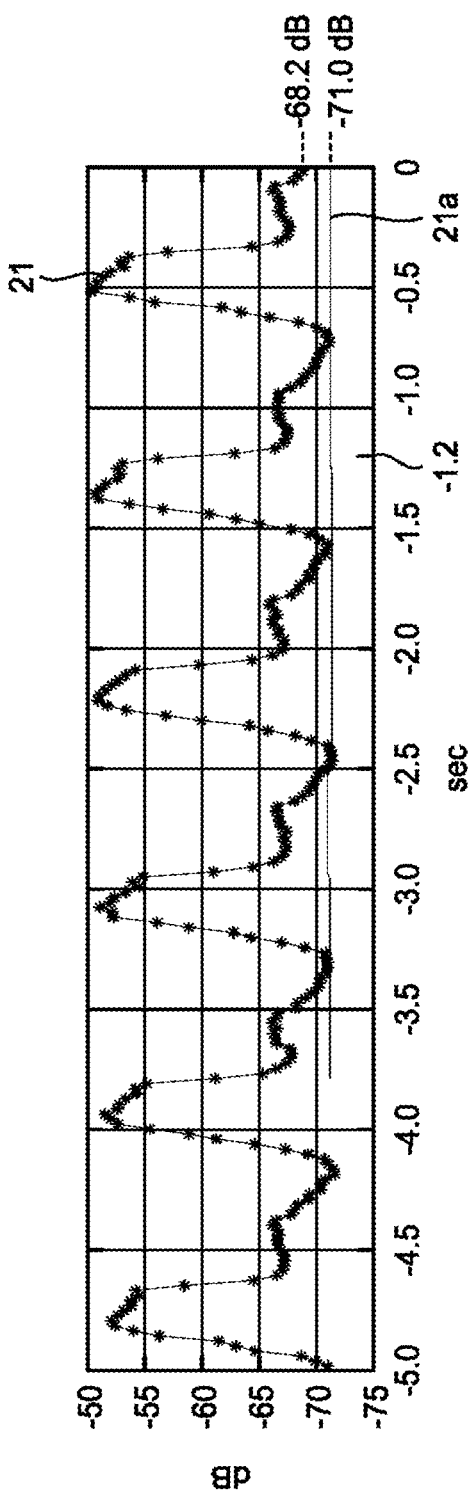
FIG. 7 is a drawing for explaining an example of a process performed by a calculating function according to the first embodiment.

FIG. 7 is a drawing for explaining an example of a process performed by the calculating function according to the first embodiment. FIG. 7 illustrates a graph 21 indicating temporal changes in the eigenvalue in the S-th place during the time period of 5 seconds from the present time (the time "0 (sec)") to the time ("−5.0 (sec)") that is 5 seconds earlier than the present time. In the graph 21, the horizontal axis expresses time (seconds (sec)). On the horizontal axis, the time in the past before the present time is indicated with negative values. The vertical axis expresses the magnitudes of the eigenvalues in the S-th place in the unit of decibels, while expressing the largest eigenvalue among the plurality of eigenvalues of the correlation matrix $R_{all}$ as 0 dB. Further, FIG. 7 illustrates a line 21a indicating the minimum value of the eigenvalue in the S-th place during each of the following time sections: the time section "from 0 (sec) to −1.2 (sec)"; the time section "from −1.2 (sec) to −2.4 (sec)"; and the time section "from −2.4 (sec) to −3.6 (sec)".

For example, at step S10, as indicated by the graph 21 and the line 21a in FIG. 7, the calculating function 142 identifies the minimum value "−71.0 (dB)" of the eigenvalue in the S-th place expressed as a decibel value, during the predetermined time period from the present time to the time that is 1.2 seconds earlier than the present time. In this manner, at step S10, the calculating function 142 identifies, for each of the medium blocks, the minimum value of the eigenvalue in the S-th place expressed as a decibel value, during the past time period of approximately one heartbeat. As explained above, for each of the medium blocks, the calculating function 142 identifies a minimum value during the predetermined time period from the present time to the time that is earlier than the present time by a predetermined length of time (e.g., 1.2 seconds), with respect to one of the plurality of eigenvalues of the correlation matrix $R_2$.

Further, at step S11, the calculating function 142 determines a final rankcut number $k_f$ for each of the medium blocks. In this situation, the rankcut number denotes, for example, the number by which the rank is reduced at the time of calculating an MTI filter matrix W (explained later). An example of the process performed at step S11 will be explained. At step S11, the calculating function 142 at first calculates, for each of the medium blocks, the difference between the decibel value of the eigenvalue in the S-th place at the present time and the minimum value of the eigenvalue in the S-th place expressed as a decibel value identified at step S10. In the following sections, the difference may be referred to as an "eigenvalue difference". More specifically, the calculating function 142 calculates the eigenvalue difference expressed as a decibel value, by subtracting the minimum value of the eigenvalue in the S-th place expressed as a decibel value identified at step S10 from the decibel value of the eigenvalue in the S-th place at the present time.

Figure 8:
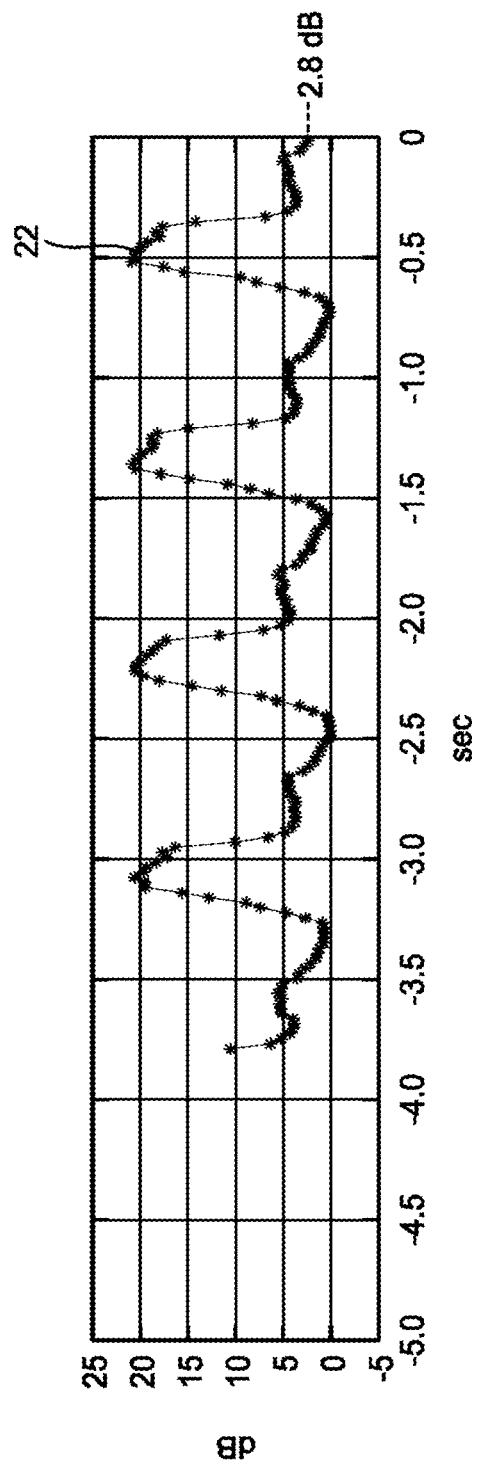
FIG. 8 is another drawing for explaining the example of the process performed by the calculating function according to the first embodiment.

In this situation, the present time (the time at present) is an example of the first point in time. The eigenvalue in the S-th place at the present time expressed as the decibel value is an example of the first eigenvalue. Further, the minimum value of the eigenvalue in the S-th place expressed as the decibel value identified at step S10 is an example of the second eigenvalue obtained at the second point in time that is earlier than the present time and is the minimum eigenvalue observed in the predetermined time span. FIG. 8 is a drawing for explaining an example of the process performed by the calculating function according to the first embodiment. FIG. 8 illustrates a graph 22. The graph 22 is a graph obtained by subtracting the minimum value of the eigenvalue in the S-th place expressed as a decibel value for each of the abovementioned time sections, from the magnitude of the eigenvalue expressed as a decibel value at each of the times indicated in the graph 21 in FIG. 7.

For example, the calculating function 142 subtracts the minimum value "−71.0 (dB)" of the eigenvalue in the S-th place expressed as a decibel value identified at step S10, from the decibel value "−68.2 (dB)" of the eigenvalue in the S-th place at the present time indicated in the graph 21 in FIG. 7. As a result, as indicated in FIG. 8, the calculating function 142 calculates the difference "2.8 (dB)" expressed as a decibel value between the decibel value "−68.2 (dB)" of the eigenvalue and the minimum value "−71.0 (dB)" of the eigenvalue expressed as a decibel value.

Further, at step S11, the calculating function 142 discretizes the eigenvalue difference by using a predetermined magnitude (e.g., 3 (dB)) of eigenvalue. For example, the calculating function 142 calculates a quotient (a numerical value) obtained by dividing the eigenvalue difference by the predetermined magnitude of eigenvalue. The calculating function 142 take the quotient into account at the time of determining the final rankcut number $k_f$.

Figure 9:
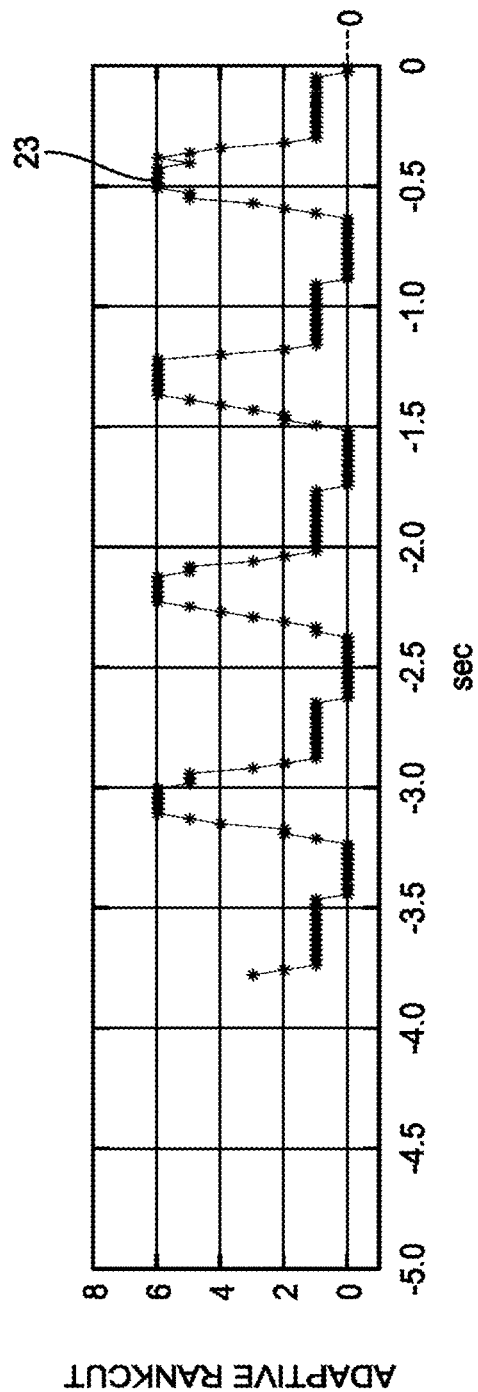
FIG. 9 is yet another drawing for explaining the example of the process performed by the calculating function according to the first embodiment.

FIG. 9 is a drawing for explaining an example of the process performed by the calculating function according to the first embodiment. FIG. 9 illustrates a graph 23. The graph 23 is a graph obtained by discretizing the eigenvalue difference at each of the times indicated in the graph 22 in FIG. 8, by using the predetermined magnitude of eigenvalue "3 (dB)" expressed as a decibel value. The predetermined magnitude of eigenvalue expressed as a decibel value does not necessarily have to be "3 (dB)". In the graph 23, the horizontal axis expresses time (seconds (sec)). On the horizontal axis, the time in the past before the present time is indicated with negative values. The vertical axis expresses the quotient (the numerical value) that is to be taken into account at the time of determining the final rankcut number $k_f$.

For example, the calculating function 142 calculates the numerical value "0" as indicated in the graph 23 in FIG. 9, by discretizing the eigenvalue difference "2.8 (dB)" corresponding to the present time indicated in the graph 22 in FIG. 8 while using the predetermined magnitude of eigenvalue "3 (dB)" expressed as a decibel value. In other words, the calculating function 142 calculates the quotient "0" obtained by dividing "2.8 (dB)" by "3 (dB)".

Further, at step S11, the calculating function 142 determines a temporary rankcut number c from the eigenvalues. For example, the calculating function 142 determines a temporary rankcut number c for each of the medium blocks by using the same method as the method described in Patent Literature (Japanese Patent Application Laid-open No. 2014-158698). For example, for each of the medium blocks, the calculating function 142 determines the temporary rankcut number c in accordance with the magnitudes of the eigenvalues of the correlation matrix $R_2$. For example, the calculating function 142 may determine, as the rankcut number c, the smallest w (where w is a natural number) that makes Aw equal to or smaller than a predetermined threshold value. Alternatively, the temporary rankcut number c may be a value that is set in advance or may be a value designated by the operator.

After that, the calculating function 142 determines the final rankcut number $k_f$ by adding the quotient (the numerical value) to the temporary rankcut number c. For example, the calculating function 142 determines the final rankcut number $k_f(c+0)$ by adding the quotient (0) calculated in the example in FIG. 9 to the temporary rankcut number c. As explained above, the calculating function 142 determines the rankcut number $k_f$ that determines the characteristic of the MTI filter on the basis of the eigenvalues of the correlation matrix $R_2$ during the predetermined time period (e.g., 1.2 seconds explained above). More specifically, the calculating function 142 determines the rankcut number $k_f$ on the basis of the eigenvalue difference expressed as a decibel value.

At step S12, the calculating function 142 calculates an eigenvector matrix $V_k$ (an L×k matrix) having rank k from the rank cut number $k_f$ (where $k_f \leq L$). In this situation, it is possible to express the eigenvector matrix $V_k$ by using Expression (7) presented below. Further, for example, $k_f = k$ is satisfied.

$$V_k = \begin{pmatrix} v_{1,1} & v_{1,2} & \cdots & v_{1,k} \\ v_{2,1} & v_{2,2} & & v_{2,k} \\ \vdots & & & \vdots \\ v_{L,1} & v_{L,2} & \cdots & v_{L,k} \end{pmatrix} \quad (7)$$

At step S13, the calculating function 142 calculates the MTI filter matrix W from the eigenvector matrix $V_k$ by using Expression (8) presented below. In Expression (8), I denotes an L×L unit matrix.

$$W = I - V_k V_k^H \quad (8)$$

As explained above, the calculating function 142 determines the MTI filter matrix W as the filter coefficient to be applied to the MTI filter, on the basis of the eigenvalues of the correlation matrix $R_2$ during the predetermined time period (e.g., 1.2 seconds explained above). Further, the calculating function 142 determines the rankcut number $k_f$ that determines the characteristic of the MTI filter on the basis of the eigenvalues of the correlation matrix $R_2$ during the predetermined time period and further determines the MTI filter matrix W on the basis of the determined rankcut number $k_f$. For example, the calculating function 142 determines the rankcut number $k_f$ that determines the characteristic of the MTI filter on the basis of a plurality of eigenvalues obtained at mutually-different points in time and further determines the MTI filter matrix W on the basis of the determined rankcut number $k_f$. In other words, the calculating function 142 determines the MTI filter matrix W on the basis of the plurality of eigenvalues obtained at the mutually-different points in time. For example, the calculating function 142 determines the MTI filter matrix W on the basis of the eigenvalue difference observed during the predetermined time period.

Further, as explained above, the calculating function 142 determines an MTI filter matrix W corresponding to each of the plurality of medium blocks, on the basis of the eigenvalues of the correlation matrix $R_2$ of the medium block. Further, the calculating function 142 determines the MTI filter matrix W on the basis of the eigenvalues of the correlation matrix $R_2$ during the time period corresponding to one heartbeat (the time span corresponding to one heartbeat) of the subject.

Step S14 is a step corresponding to the MTI filter processing function 143. Step S14 is a step at which the MTI filter processing function 143 is realized as a result of the Doppler processing circuitry 14 invoking and executing a predetermined program corresponding to the MTI filter processing function 143 from the internal storage circuitry 17. At step S14, for each of the medium blocks, the MTI filter processing function 143 applies the MTI filter to the packet column vector data $x_i$ at each of the points, by using Expression (9) presented below. In other words, the MTI filter processing function 143 uses the packet column vector data $x_i$ in the position i as input data and calculates, for each of the medium blocks, packet column vector data $y_i$, which is output data of the position i, from the input data and the MTI filter matrix W, by using Expression (9) presented below. The quantity of the elements in the packet column vector data $y_i$ is "L".

$$y_i = W x_i \quad (9)$$

For example, to the data of the medium block made up of the 4×4 small blocks indicated in pattern (A) in FIG. 6, the MTI filter processing function 143 applies an MTI filter calculated from the data of the medium block indicated in pattern (A) in FIG. 6.

Steps S15 and S16 are steps corresponding to the estimating function 144. Steps S15 and S16 are steps at which the estimating function 144 is realized as a result of the Doppler processing circuitry 14 invoking and executing a predetermined program corresponding to the estimating function 144 from the internal storage circuitry 17. At steps S15 and S16, the estimating function 144 estimates moving member information from the data sequence by performing a statistical calculation. For example, the estimating function 144 estimates the moving member information in each of the plurality of regions into which the scan range formed with the plurality of scanning lines is divided, by using a statistical characteristic calculated from the region.

More specifically, at step S15, the estimating function 144 estimates power $P_i$ in the position i, by using Expression (10) presented below, from the data of the medium block to which the MTI filter was applied at step S14. In this situation, the estimating function 144 estimates the power $P_i$ as a value prior to a logarithmic compression. In Expression (10), j denotes an index indicating an element number of a column vector, whereas $y_{i,j}$ denotes a j-th element in the packet column vector data $y_i$.

$$P_i = \sum_{j=1}^{L} |y_{i,j}|^2 \quad (10)$$

Further, at step S16, the estimating function 144 estimates velocity $V_i$ in the position i by using Expression (11) presented below, from the data of the medium block to which the MTI filter was applied at step S14. In Expression (11), "angle" denotes a mathematical function configured to output an argument of a complex number in the range of $-\pi$ to $\pi$. Further, in Expression (11), the symbol "*" (asterisk) denotes the complex conjugate.

$$V_i = \text{angle}\left(\sum_{j=1}^{L-1} y_{i,j} * y_{i,j+1}\right) \quad (11)$$

The estimating function 144 may interchange the processing order between step S15 and step S16 or may perform these steps at the same time.

Step S17 is a step corresponding to the region combining function 146. Step S17 is a step at which the region combining function 146 is realized as a result of the Doppler processing circuitry 14 invoking and executing a predetermined program corresponding to the region combining function 146 from the internal storage circuitry 17. At step S17, the region combining function 146 perform a weighted addition. For example, the region combining function 146 performs a region combining process on power values and a region combining process on velocity values. For example, the region combining function 146 interpolates pixels, by performing multiplication using a weighted coefficient corresponding to the position by implementing a bilinear method that uses the weighted coefficient and adding together pieces of data in mutually the same position.

Step S18 is a step realized by the image generating circuitry 15. At step S18, the image generating circuitry 15 generates blood flow image data (color Doppler image data) from the moving member information. For example, the image generating circuitry 15 generates blood flow image data (power image data) by performing a logarithmic compression on the power $P_i$ estimated at step S15. Further, the image generating circuitry 15 generates blood flow image data (velocity image data) based on the velocity $V_i$ estimated at step S16.

Step S19 is a step realized by the processing circuitry 18. At step S19, the processing circuitry 18 causes the monitor 2 to display one or more of the blood flow images represented by the blood flow image data, and the process is thus ended.

Figure 10A:
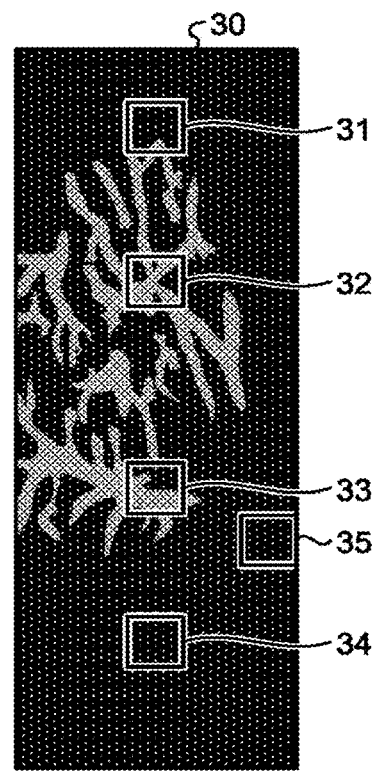
FIG. 10A is a drawing illustrating an example of a blood flow image represented by blood flow image data generated as a result of the ultrasound diagnosis apparatus according to the first embodiment performing the processes illustrated in FIG. 5.
Figure 10B:
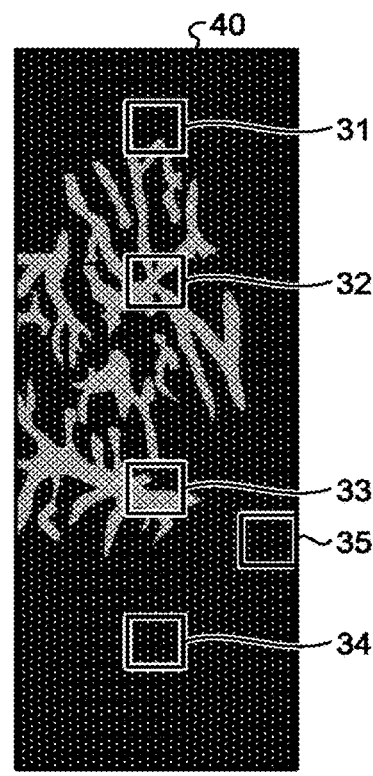
FIG. 10B is another drawing illustrating an example of a blood flow image represented by blood flow image data generated as a result of the ultrasound diagnosis apparatus according to the first embodiment performing the processes illustrated in FIG. 5.

FIGS. 10A and 10B are drawings illustrating examples of the blood flow images represented by the blood flow image data generated as a result of the ultrasound diagnosis apparatus according to the first embodiment performing the processes illustrated in FIG. 5.

Blood flow images 30 and 40 illustrated in FIGS. 10A and 10B are images rendering blood flow information of the liver of the subject P. The blood flow images 30 and 40 are each a power image generated from the power image data. For example, each of the blood flow images 30 and 40 is an image generated from the blood flow image data based on the reflected-wave signals acquired by the ultrasound probe 1 being a convex probe and is displayed on the monitor 2 without having a coordinate transformation performed thereon. Further, on the outside of the range of the blood flow images 30 and 40, a cardiac wall, the diaphragm, and the like are present as reflection sources of a side lobe.

In this situation, at the time of generating the blood flow images 30 and 40, the correlation matrix $R_2$ is calculated for each of the plurality of medium blocks. The five reference numerals 31 to 35 in FIGS. 10A and 10B indicate five medium blocks among the plurality of medium blocks.

FIG. 10C is a graph illustrating an example of temporal changes in the magnitude of the eigenvalue in the S-th place in each of the medium blocks. FIG. 10C illustrates five graphs 31b to 35b indicating temporal changes over 5 seconds in the magnitude of the eigenvalue in the S-th place in the five regions 31 to 35, respectively.

More specifically, in FIG. 10C, the graph 31b is a graph indicating temporal changes in the magnitude of the eigenvalue in the S-th place in the region 31; the graph 32b is a graph indicating temporal changes in the magnitude of the eigenvalue in the S-th place in the region 32; the graph 33b is a graph indicating temporal changes in the magnitude of the eigenvalue in the S-th place in the region 33; the graph 34b is a graph indicating temporal changes in the magnitude of the eigenvalue in the S-th place in the region 34; and the graph 35b is a graph indicating temporal changes in the magnitude of the eigenvalue in the S-th place in a region 35.

Further, in FIG. 10C, the graph 36b is a graph indicating temporal changes in the magnitude of the eigenvalue in the S-th place among a plurality of eigenvalues of a correlation matrix obtained by calculating an ensemble average of all the correlation matrices $R_2$ of all the medium blocks.

In the graphs, the horizontal axis expresses time (seconds (sec)). On the horizontal axis, the time in the past before the present time is indicated with negative values. For example, the time "0 (sec)" indicates the present time (the point in time). Further, for example, the time "−0.5 (sec)" indicates the time (the point in time) in the past that is 0.5 seconds earlier than the present time. The vertical axis expresses the magnitude of the eigenvalue in the S-th place for each of the medium blocks in the unit of decibels, while expressing the largest eigenvalue among the plurality of eigenvalues of a correlation matrix obtained by calculating an ensemble average of all the correlation matrices $R_2$ of all the medium blocks as 0 dB.

For example, a fifth temporal phase corresponding to the blood flow image 30 illustrated in FIG. 10A corresponds to the time "−3.3 (sec)" in FIG. 10C. Further, a sixth temporal phase corresponding to the blood flow image 40 illustrated in FIG. 10B corresponds to the time "−3.07 (sec)" in FIG. 10C. In other words, the blood flow image data representing the blood flow image 30 is the data generated at the time "−3.3 (sec)", whereas the blood flow image data representing the blood flow image 40 is the data generated at the time "−3.07 (sec)".

The graphs 31b to 36b periodically fluctuate in synchronization with the cardiac cycle of the subject P. Further, the graph 35b periodically exhibits the sixth temporal phase in which the eigenvalue is relative large and the fifth temporal phase in which the eigenvalue is relatively small. As indicated in the graph 35b, in the sixth temporal phase (e.g., the time "−3.07 (sec)") in which the eigenvalue is relatively large, it is considered that the motion of the cardiac wall is relatively large, for example. However, as indicated in FIG. 10B, the region 35 in the blood flow image 40 in the sixth temporal phase contains almost no clutter.

Figure 11:
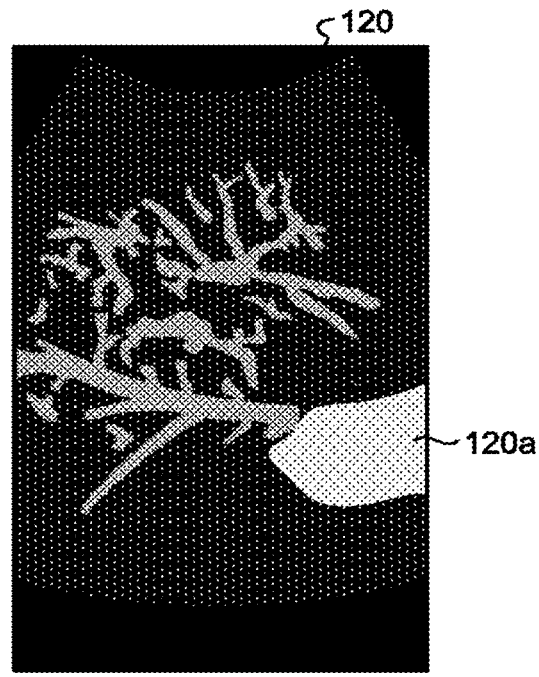
FIG. 11 is a drawing illustrating a blood flow image represented by blood flow image data generated in the first comparison example.
Figure 12:
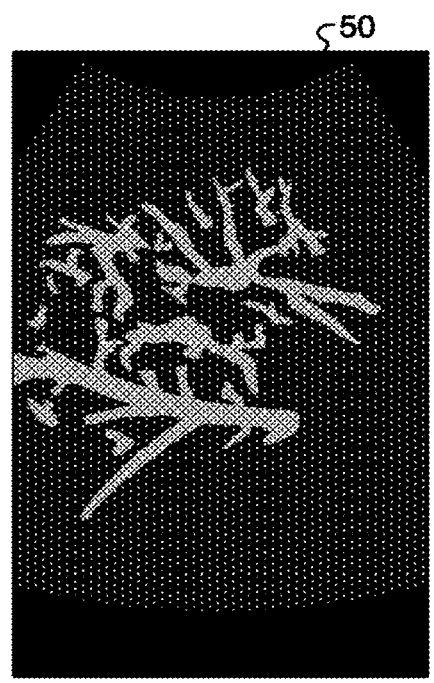
FIG. 12 is a drawing illustrating a blood flow image represented by blood flow image data generated in the first embodiment.

FIG. 11 is a drawing illustrating a blood flow image represented by the blood flow image data generated in the first comparison example. FIG. 12 is a drawing illustrating a blood flow image represented by the blood flow image data generated according to the first embodiment.

More specifically, FIG. 11 is a drawing illustrating a blood flow image 120 displayed on a monitor after performing a coordinate transformation on the blood flow image 104 in the temporal phase (the fourth temporal phase) in which the eigenvalue is relatively large illustrated in FIG. 3C. FIG. 12 is a drawing illustrating a blood flow image 50 displayed on the monitor 2 after performing a coordinate transformation on the blood flow image 40 in the temporal phase (the sixth temporal phase) in which the eigenvalue is relatively large illustrated in FIG. 10B.

As illustrated in FIG. 11, in the first comparison example, the blood flow image 120 contains clutter 120a. In contrast, as illustrated in FIG. 12, in the first embodiment, the blood flow image 50 contains no clutter or the clutter contained in the blood flow image 50 is significantly reduced. Consequently, according to the first embodiment, it is possible to suppress the clutter component occurring as a result of a side lobe being reflected on a highly reflective member that moves periodically and moves at relatively high speed, like the pulsating motion of the heart. Further, according to the first embodiment, it is possible to generate the MTI filter capable of suppressing such a clutter component.

In the first embodiment described above, the example is explained in which the ultrasound diagnosis apparatus performs the ultrasound scan on the liver; however, the ultrasound diagnosis apparatus may perform an ultrasound scan on another organ besides the liver that is impacted by the periodical pulsating motion of the heart. For example, the ultrasound diagnosis apparatus may perform an ultrasound scan on the thyroid gland that is positioned in the vicinity of the carotid arteries that move periodically.

Further, in the first embodiment described above, the block dividing function 145 is configured to divide the imaging target range into the small blocks as illustrated in FIG. 6. As a result, the correlation matrix calculating function 141 is able to calculate the correlation matrix of each of the medium blocks by calculating an arithmetic mean of the correlation matrices of the small blocks. Further, because the medium blocks overlap with one another in units of the small blocks, none of the correlation matrix calculations is wasteful. Further, by having the spatial data and the packet data stored in a memory in units of the small blocks, it is possible to achieve high cache efficiency when the MTI filter matrix calculation is performed by a CPU.

Further, in the first embodiment described above, the example is explained in which the block dividing function 145 is configured to form the medium blocks in such a manner that a part of each of the medium blocks overlaps with a part of each of the other medium blocks; however, possible embodiments are not limited to this example. For instance, the block dividing function 145 may form the medium blocks in such a manner that no part of each of the medium blocks overlaps with a part of the other medium blocks.

Further, in the embodiments described above, the estimating function 144 is configured to extract the moving member information from the data to which the MTI filters W have been applied, the MTI filters W being generated in correspondence with the plurality of medium blocks into which the imaging target range is divided; however, possible embodiments are not limited to this example. For instance, the estimating function 144 may extract the moving member information from data to which an MTI filter generated for the entire imaging target range is applied. In other words, the correlation matrix calculating function 141 may be configured to calculate a correlation matrix of the entire imaging target range from a data sequence of the reflected-wave data in mutually the same position acquired by performing an ultrasound scan on the entire imaging target range formed with a plurality of scanning lines. Further, the calculating function 142 may determine a filter coefficient to be applied to the MTI filter on the basis of the eigenvalues of a correlation matrix during a predetermined time period.

Further, in the embodiments described above, the example is explained in which the calculating function 142 is configured to determine the rankcut number $k_f$ from the correlation matrix $R_2$ of each of the medium blocks; however, possible embodiments are not limited to this example. For instance, the calculating function 142 may determine a rankcut number $k_f$ from the correlation matrix $R_{all}$ of the entire imaging target range.

In the embodiments described above, the example is explained in which the calculating function 142 identifies the minimum value of the eigenvalue in the S-th place among the plurality of eigenvalues in the S-th place of the correlation matrix $R_2$ calculated during the predetermined time span for each of the medium blocks; however, possible embodiments are not limited to this example. For instance, the calculating function 142 may identify a maximum value of the eigenvalue in the S-th place among the plurality of eigenvalues in the S-th place of the correlation matrix $R_2$ calculated during a predetermined time span for each of the medium blocks. In that situation, the calculating function 142 calculates an eigenvalue difference by subtracting the maximum value of the eigenvalue in the S-th place expressed as a decibel value, from the eigenvalue in the S-th place at the present time expressed as a decibel value. The maximum value of the eigenvalue in the S-th place expressed as the decibel value is an example of the second eigenvalue obtained at a point in time earlier than the present time and is the maximum eigenvalue observed in the predetermined time span.

Modification Examples of First Embodiment

In the first embodiment above, the example is explained in which the Doppler processing circuitry 14 is configured to calculate the eigenvalues and the eigenvector by performing the eigenvalue decomposition on the correlation matrix and to determine the MTI filter matrix W on the basis of the eigenvalues and the eigenvectors. However, another arrangement is also acceptable in which the Doppler processing circuitry 14 calculates singular values and right singular vectors by performing a singular value decomposition on a correlation matrix, so as to determine an MTI filter matrix W on the basis of the singular values and the right singular vectors. Thus, this modification example will be explained as a modification example of the first embodiment.

In the modification example of the first embodiment, an example will be explained in which a singular value decomposition is performed on a matrix $X^H$, as a statistical characteristic. For example, when the quantity of all of the location points in each of the small blocks is expressed as N, while the packet size is expressed as L, it is possible to express Expression (1) above with Expression (12) presented below by using an L×N matrix X of which the column vector is expressed as $x_i$.

$$R_1 = \frac{1}{N} XX^H \qquad (12)$$

The calculating function 142 included in the Doppler processing circuitry 14 performs a singular value decomposition on the matrix $X^H$ by using Expression (13) presented below.

$$X^H = P \Lambda Q^H \qquad (13)$$

In Expression (13), the column vectors of the matrix Q are right singular vectors.

By assigning Expression (13) to Expression (12), it is possible to express the correlation matrix $R_1$ by using Expression (14) presented below, because P is a unitary matrix.

$$R_1 = \qquad (14)$$
$$\frac{1}{N} XX^H = \frac{1}{N}(P\Lambda Q^H)^H (P\Lambda Q^H) = \frac{1}{N} Q\Lambda^H P^H P \Lambda Q^H = \frac{1}{N} Q\Lambda^H \Lambda Q^H$$

As Expression (4) is compared with Expression (14), it is possible to express the matrix V by using Expression (15) presented below and to express the matrix D by using Expression (16) presented below.

$$V = Q \tag{15}$$

$$D = \frac{1}{N} \Lambda^H \Lambda \tag{16}$$

In Expression (16), $\Lambda$ denotes an N×L matrix, whereas the eigenvalues of the Hermitian matrix $R_1$ are positive. Accordingly, it is possible to express the matrix $\Lambda$ by using Expression (17) presented below.

$$\Lambda = \sqrt{N} \begin{pmatrix} \sqrt{\lambda_1} & 0 & \cdots & 0 \\ 0 & \sqrt{\lambda_2} & & 0 \\ \vdots & & \ddots & \vdots \\ 0 & 0 & \cdots & \sqrt{\lambda_L} \\ 0 & 0 & \cdots & 0 \\ \vdots & \vdots & \ddots & \vdots \\ 0 & 0 & \cdots & 0 \end{pmatrix} \tag{17}$$

The square roots of the values of the elements ($\lambda_n$ where n=1, 2, ..., and L) of the matrix $\Lambda$ are singular values of the matrix $X^H$. That is, the singular values are non-negative square roots of the eigenvalues of the correlation matrix $R_{all}$.

Further, the calculating function 142 determines an MTI filter matrix W, on the basis of the singular values and the right singular vectors during a predetermined time period (e.g., 1.2 seconds). For example, the calculating function 142 determines the rankcut number $k_f$ on the basis of the singular values and the right singular vectors during the predetermined time period by using the same method as the method which determines the rankcut number $k_f$ in the first embodiment in consideration of differences between the singular values and the eigenvalues. Further, the calculating function 142 determines the MTI filter matrix W on the basis of the determined rankcut number $k_f$.

In that situation, the MTI filter processing function 143 applies the MTI filter W to the packet column vector data X at each of the points by using Expression (18) presented below.

$$Y = WX \tag{18}$$

As explained above, in the modification example of the first embodiment, the Doppler processing circuitry 14 determines the MTI filter matrix W by performing the singular value decomposition on the matrix $X^H$.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in storage circuitry. Instead of the programs being saved in the storage circuitry, the programs may directly be incorporated into the circuits of one or more processors. In that situation, the one or more processors realize the functions by reading and executing the programs incorporated in the circuits thereof. The processors of the present embodiments do not each necessarily have to be configured as a single circuit. It is also acceptable to structure one processor by combining together two or more independent circuits so as to realize the functions thereof. Further, two or more of the constituent elements illustrated in FIG. 1 may be integrated into one processor so as to realize the functions thereof.

Further, the constituent elements of the apparatuses and the devices illustrated in the drawings in the explanations of the above embodiments are based on functional concepts. Thus, it is not necessary to physically configure the constituent elements as indicated in the drawings. In other words, specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program analyzed and executed by the CPU or may be realized as hardware using wired logic.

Further, the medical image processing methods explained in the above embodiments may be realized by causing a computer such as a personal computer or a workstation to execute a medical image processing program prepared in advance. The computer such as the personal computer or the workstation is an example of the medical image processing apparatus. The medical image processing program may be distributed via a network such as the Internet. Further, the medical image processing program may be recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like, so as to be executed as being read from the recording medium by a computer.

According to at least one aspect of the embodiments described above, it is possible to generate the MTI filter capable of suppressing the clutter component that may occur as a result of the side lobe being reflected by a highly reflective member that moves periodically and moves at relatively high speed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
processing circuitry configured:
  to sequentially obtain eigenvalues of a correlation matrix of a scan range, the correlation matrix being obtained from a data sequence of reflected-wave data in a mutually same position acquired by performing an ultrasound scan on the scan range formed with a plurality of scanning lines; and
  to determine a filter coefficient to be applied to a Moving Target Indicator (MTI) filter, on a basis of the plurality of eigenvalues obtained at mutually-different points in time, wherein
the processing circuitry
  identifies a minimum value of an eigenvalue among the plurality of eigenvalues in a predetermined time period from a present time to a time that is a predetermined time earlier than the present time, calculates a difference between the minimum value and an eigenvalue at the present time, and determines the filter coefficient based on the difference.

2. The ultrasound diagnosis apparatus according to claim 1, wherein the processing circuitry determines the filter coefficient on a basis of a result of comparing the plurality of eigenvalues obtained at the mutually-different points in time with one another.

3. The ultrasound diagnosis apparatus according to claim 1, wherein the plurality of eigenvalues include a first eigenvalue obtained at a first point in time and a second eigenvalue obtained at a second point in time earlier than the first point in time, and the second eigenvalue is one of a minimum eigenvalue and a maximum eigenvalue observed in a predetermined time span.

4. The ultrasound diagnosis apparatus according to claim 3, wherein the processing circuitry determines the filter coefficient on a basis of a difference between the first eigenvalue and the second eigenvalue.

5. The ultrasound diagnosis apparatus according to claim 1, wherein the processing circuitry determines a rankcut number that determines a characteristic of the MTI filter, on a basis of the plurality of eigenvalues, and the processing circuitry determines the filter coefficient on a basis of the determined rankcut number.

6. The ultrasound diagnosis apparatus according to claim 1, wherein the processing circuitry calculates a correlation matrix of each of a plurality of regions into which the scan range is divided, and the processing circuitry determines a filter coefficient corresponding to each of the plurality of regions on a basis of eigenvalues of the correlation matrix of the region.

7. The ultrasound diagnosis apparatus according to claim 1, wherein the processing circuitry determines the filter coefficient on a basis of the eigenvalues of the correlation matrix during a time span corresponding to one heartbeat of a subject.

8. The ultrasound diagnosis apparatus according to claim 1, wherein the processing circuitry obtains the correlation matrix from the data sequence of the reflected-wave data in mutually the same position acquired over a plurality of frames by performing the ultrasound scan by which a same scanning line is scanned once in one frame.

9. A medical image processing apparatus comprising:
processing circuitry configured:
to sequentially obtain either eigenvalues or singular values of a correlation matrix of a scan range, the correlation matrix being obtained from a data sequence of reflected-wave data in a mutually same position acquired by performing an ultrasound scan on the scan range formed with a plurality of scanning lines; and to determine a filter coefficient to be applied to an MTI filter, on a basis of one selected from between the plurality of eigenvalues and the plurality of singular values obtained at mutually-different points in time, wherein the processing circuitry identifies a minimum value of an eigenvalue among the plurality of eigenvalues in a predetermined time period from a present time to a time that is a predetermined time earlier than the present time, calculates a difference between the minimum value and an eigenvalue at the present time, and determines the filter coefficient based on the difference.

10. A non-transitory computer-readable storage medium storing therein a program configured to cause a computer to execute processes of:

sequentially obtaining either eigenvalues or singular values of a correlation matrix of a scan range, the correlation matrix being obtained from a data sequence of reflected-wave data in a mutually same position acquired by performing an ultrasound scan on the scan range formed with a plurality of scanning lines; and determining a filter coefficient to be applied to an MTI filter, on a basis of one selected from between the plurality of eigenvalues and the plurality of singular values obtained at mutually-different points in time, wherein the determining the filter coefficient comprises identifying a minimum value of an eigenvalue among the plurality of eigenvalues in a predetermined time period from a present time to a time that is a predetermined time earlier than the present time, calculating a difference between the minimum value and an eigenvalue at the present time, and determining the filter coefficient based on the difference.

* * * * *